US007429480B2

(12) United States Patent
Kou et al.

(10) Patent No.: US 7,429,480 B2
(45) Date of Patent: Sep. 30, 2008

(54) PROMOTER SEQUENCES FROM WSSV IMMEDIATE EARLY GENES AND THEIR USES IN RECOMBINANT DNA TECHNIQUES

(75) Inventors: Guang-Hsiung Kou, Taipei (TW); Chu-Fang Lo, Taipei (TW); Wang-Jing Liu, Taipei (TW)

(73) Assignee: National Taiwan University, Taipei (TW)

( * ) Notice: Subject to any disclaimer, the term of this patent is extended or adjusted under 35 U.S.C. 154(b) by 530 days.

(21) Appl. No.: 11/032,682

(22) Filed: Jan. 10, 2005

(65) Prior Publication Data

US 2006/0154369 A1    Jul. 13, 2006

(51) Int. Cl.
*C12N 5/00* (2006.01)
(52) U.S. Cl. .................. 435/320.1; 435/325; 536/24.1; 536/24.33
(58) Field of Classification Search ................ None
See application file for complete search history.

(56) References Cited

U.S. PATENT DOCUMENTS

| 5,077,214 | A | 12/1991 | Guarino et al. |
| 5,162,222 | A | 11/1992 | Guarino et al. |
| 5,168,062 | A | 12/1992 | Stinski |
| 5,385,839 | A | 1/1995 | Stinski |
| 2002/0116723 | A1 | 8/2002 | Grigliatti et al. |
| 2003/0108524 | A1 | 6/2003 | Diagana et al. |
| 2003/0108863 | A1 | 6/2003 | Ball et al. |
| 2003/0229046 | A1 | 12/2003 | Kim et al. |
| 2004/0082531 | A1 | 4/2004 | Catchpole et al. |
| 2004/0161841 | A1 | 8/2004 | Dohner et al. |
| 2004/0197313 | A1 | 10/2004 | Wang et al. |
| 2006/0242719 | A1* | 10/2006 | Sun et al. ............. 800/13 |

FOREIGN PATENT DOCUMENTS

| WO | WO 99/61636 | 12/1999 |
| WO | WO 00/40737 | 7/2000 |
| WO | WO 01/05992 | 1/2001 |

OTHER PUBLICATIONS

Gary W. Blissard. "Baculovirus—insect cell interactions". Cytotechnology 20:73-93, 1996.
Gary W. Blissard et al. "A Synthetic Early Promoter from a Baculovirus: Roles of the TATA Box and Conserved Start Site CAGT Sequence in Basal Levels of Transcription". Virology 190:783-793, 1992.
Gary W. Blissard et al. "Baculovirus Diversity and Molecular Biology". Annu. Rev. Entomol. 35:127-155, 1990.
Gary W. Blissard et al. "Baculovirus gp64 Gene Expression: Analysis of Sequences Modulating Early Transcription and Transactivation by IE1". Journal of Virology 65(11):5820-5827, Nov. 1991.
Li-Li Chen et al. "Transcriptional Analysis of the DNA Polymerase Gene of Shrimp White Spot Syndrome Virus". Virology 301:136-147, 2002.
Lucy Cherbas et al. "The Arthropod Initiator: The Capsite Consensus Plays an Important Role in Transcription". Insect Biochem. Mol. Biol. 23(1):81-90, 1993.
Julie A. Dickson et al. "Identification of Upstream Promoter Elements Mediating Early Transcription from the 35,000-Molecular-Weight Protein Gene of *Autographa californica* Nuclear Polyhedrosis Virus". Journal of Virology 65(8):4006-4016, Aug. 1991.
T. W. Flegal. Special topic review: Major viral diseases of the black tiger prawn (*Penaeus monodon*) in Thailand. World Journal of Microbiology & Biotechnology 13:433-442, 1997.
Lois K. Miller et al. "The Baculoviruses". Chapter 6, pp. 141-169. Plenum Press/Plenum Publishing Corporation, New York. 1997.
P. D. Friesen et al. "The Regulation of Baculovirus Gene Expression". Current Topics in Microbiology and Immunology, Springer-Verlag, Berlin, Heidelberg, 131:31-49, 1986.
Michael A. Frohman et al. "Rapid Production of Full-Length cDNA's from Rare Transcripts: Amplification Using a Single Gene-Specific Oligonucleotide Primer". Proc. Nat. Acad. Sci. USA 85(23): 8998-9002, Dec. 1, 1998.
Linda A. Guarino et al. "Nucleotide Sequence and Characterization of the 39K Gene Region of *Autographa californica* Nuclear Polyhedrosis Virus". Virology 179:1-8, 1990.
Linda A. Guarino et al. "Regulation of Delayed-Early Gene Transcription by Dual TATA Boxes". Journal of Virology 66(6):3733-3739, Jun. 1992.
Dwayne D. Hegedus et al. "A series of broad host range shuttle vectors for constitutive and inducible expression of heterologous proteins in insect cell lines". Gene 207:241-249, 1998.
Robert W. Honess et al. "Regulation of Herpesvirus Macromolecular Synthesis I. Cascade Regulation of the Synthesis of Three Groups of Viral Proteins". Journal of Virology 14(1):8-19, Jul. 1974.
Philip H. Kogan et al. "A Baculovirus gp64 Early Promoter Is Activated by Host Transcription Factor Binding to CACGTG and GATA Elements". Journal of Virology 68(2):813-822, Feb. 1994.
Donald V. Lightner, Ph.D. "A Handbook of Shrimp Pathology and Diagnostic Procedures for Diseases of Cultured Penaeid Shrimp—Section 3: Viruses". The World Aquaculture Society, pp. 1-8, 1996.
Wang-Jing Liu et al. "Cloning, Characterization, and Phylogenetic Analysis of a Shrimp White Spot Syndrome Virus Gene That Encodes a Protein Kinase". Virology 289:362-377, 2001.
Chu-Fang Lo et al. "Major Viral Diseases of *Penaeus monodon* in Taiwan". J. Fish. Soc. Taiwan 30(1):1-13, 2003.

(Continued)

*Primary Examiner*—James Ketter
(74) *Attorney, Agent, or Firm*—Occhiuti Rohlicek & Tsao LLP

(57) ABSTRACT

Disclosed herein are isolated promoter-regulatory regions from a newly identified WSSV immediate early (IE) gene, ie1 (immediate early gene #1), which exhibit promoter activity to drive the transcription of a target gene in non-native host cells. The isolated promoter-regulatory regions can be used in the construction of a variety of recombinant expression vectors for transforming a broad spectrum of host cells.

19 Claims, 5 Drawing Sheets

OTHER PUBLICATIONS

Chu-Fang Lo et al. "White spot syndrome Baculovirus (WSBV) detected in cultured and captured shrimp, crabs and other anthropods". Diseases of Aquatic Organisms 27:215-225, Dec. 12, 1996.

Cynthia T. McMurray et al. "Hairpin Formation Within the Enhancer Region of the Human Enkephalin Gene". Proc. Natl. Acad. Sci. USA, 88:666-670, Jan. 1991.

Timothy D. Morris et al. "Mutational analysis of a Baculovirus major late promoter". Gene 140(2):147-53, Mar. 25, 1994.

Steven S. Pullen et al. "Early Transcription of the *ie-1* Transregulator Gene of *Autographa californica* Nuclear Polyhedrosis Virus Is Regulated by DNA Sequences within Its 5 Noncoding Leader Region". Journal of Virology 69(1):156-165, Jan. 1995.

Victoria A. Olson et al. "Baculovirus Transregulator IE1 Requires a Dimeric Nuclear Localization Element for Nuclear Import and Promoter Activation". Journal of Virology 76(18):9505-9515, Sep. 2002.

M. A. Mayo. "A summary of taxonomic changes recently approved by ICTV". Arch. Virol. 147(8):1655-1656, 2002.

Li-Li Chen et al. "Transcriptional Analysis of the DNA Polymerase Gene of Shrimp White Spot Syndrome Virus". Virology 301:136-147, 2002.

Eric B. Carstens et al. "Identification and molecular characterization of the Baculovirus CfMNPV early genes: *ie-1, ie-2 and pe38\**". Virus Research 83:13-30, 2002.

Robert L. Harrison et al. "Comparative analysis of the genomes of *Rachiplusia ou* and *Autographa californica* multiple nucleopolyhedroviruses". Journal of General Virology 84:1827-1842, 2003.

Hendrik Marks et al. "Transcriptional analysis of the white spot syndrome virus major virion protein genes". Journal of General Virology 84:1517-1523, 2003.

Victoria A. Olson et al. "The Highly Conserved Basic Domain I of Baculovirus IE1 Is Required for *hr* Enhancer DNA Binding and *hr*-Dependent Transactivation". Journal of Virology 77(10):5668-5677, May 2003.

Alejandra Garcia-Maruniak et al. "Sequence Analysis of the Genome of the *Neodiprion sertifer* Nucleopolydedrovirus". Journal of Virology 78(13):7036-7051, Jul. 2004.

Jiann-Horng Leu et al. "The Unique Stacked Rings in the Nucleocapsid of the White Spot Syndrome Virus Virion Are Formed by the Major Structural Protein VP664, the Largest Viral Structural Protein Ever Found". Journal of Virology 79(1):140-149, Jan. 2005.

Han-Ching Wang et al. "DNA Microarrays of the White Spot Syndrome Virus Genome: Genes Expressed in the Gills of Infected Shrimp". Manuscript for the Proceedings of Marine Biotechnology Conference 2003.

Charlotte Rasmussen et al. "Structure-Function Analysis of the *Autographa californica* Multinucleocapsid Nuclear Polyhedrosis Virus Homologous Region Palindromes". Virology 224:235-245, 1996.

Martin G. Reese et al. "New Neural Network Algorithms for Improved Eukaryotic Promoter Site Recognition". Retrieved from the Internet: <URL: http://www/fruitfly.org~martinr/doc/hh-abstract.html>, Accessed 2005.

Martin G. Reese et al. "Large Scale Sequencing Specific Neural Networks for Promoter and Splice Site Recognition". Retrieved from the Internet: <URL: http://www/fruitfly.org~martinr/doc/psb-abstract.html>, Accessed 2005.

Jyh-Ming Tsai et al. "Genomic and Proteomic Analysis of Thirty-Nine Structural Proteins of Shrimp White Spot Syndrome Virus". Journal of Virology 78(20):11360-11370, Oct. 2004.

Meng-Feng Tsai et al. "Identification and Characterization of a Shrimp White Spot Syndrome Virus (WSSV) Gene That Encodes a Novel Chimeric Polypeptide of Cellular-Type Thymidine Kinase and Thymidylate Kinase". Virology 277:100-110, 2000.

Y-G. Zhao et al. "Comparative analysis of promoters for transient gene expression in cultured mosquito cells". Insect Molecular Biology 8(1):31-38, 1990.

Invitrogen™ Life Technologies. "InsectSelect™ System with pIZ/V5-His—Version F". Cotolog pp. 1-36, Jul. 12, 2002.

Linda A. Guarino et al. "Functional Mapping of a *trans*-Activating Gene Required for Expression of a Baculovirus Delayed-Early Gene". Journal of Virology 57(2):563-571, 1986.

Andrew K. Cheung. "DNA nucleotide sequence analysis of the immediate-early gene of pseudorabies virus". Nucleic Acid Research 17(12):4637-4646, May 11, 1989.

Steven S. Pullen et al. "The CAGT Motif Functions as an Initiator Element during Early Transcription of the Baculovirus Transregulator *ie-1*". Journal of Virology 69(6):3475-3583, Jun. 1995.

M. Keith Barnhardt et al. "Function of the Human T-Cell Leukemia Virus Type 1 21-Base-Pair Repeats in Basal Transcription". Journal of Virology 71(1):337-344, Jan. 1997.

Tom A. Pfeifer et al. "Baculovirus immediate-early promoter-mediated expression of the Zeocin™ resistance gene for use as a dominant selectable marker in Dipteran and Lepidopteran insect cell lines". Gene 188:183-190, 1997.

Fan Xiu Zhu et al. "Identification of the Immeidate-Early Transcripts of Kaposi's Sarcoma-Associated Herpesvirus". Journal of Virology 73(7):5556-5567, Jul. 1999.

Meng-Feng Tsai et al. "Long-term presence of white spot syndrome virus (WSSV) in a cultivated shrimp population without disease outbreaks". Diseases of Aquatic Organisms 38:107-114, Nov. 8, 1999.

E. A. van Strien et al. "Characteristics of the transactivator gene *ie1* of *Spodoptera exigua* multiple nucleopolyhedrovirus". Arch. Virol. 145:2115-2133, 2000.

K. Kojima et al. "Tandem repetition of Baculovirus ie1 promoter results in upregulation of transcription". Arch. Virol. 146:1407-1414, 2001.

Feng Yang et al. "Complete Genome Sequence of the Shrimp White Spot Bacilliform Virus". Journal of Virology 75(23):11811-11820, Dec. 2001.

Hossain et al., "Characterization of ORF89—A latency-related gene of white spot syndrome virus" *Virology* 2004 325(1):106-115.

\* cited by examiner

```
gatgatggtgatgtttctaggcaagaaaaaggtctcccgataataaaattgccattggatatcagtcgttttgcctttgtaacacaaggagattcgtcca  -1964
      126 2k-F
caaaatacttgtatccgaaagatatgtcaaaaggttcaagtggtgcagattttttcatttcagccacgtaatcagaggtgatattgacgattcttgaaaa  -1864
               GATA                                                      GATA
gagcctgaatctaataacactcgaacattttcaacgtagaaaacaataccacttcttgcagaactagtagacttttcaggctagccaaaacaccgtcc  -1764 aacttcttgatccttctcataaccttctctctttcttcctcagcctgttcctttgaagtaaacttgaatccagttctgctgtcatcaccagtgccaaact  -1664 tgatgccgtgcgtctcgcgtctcaaaaatccattatccatagagaccagaagagaatattttacgaacaaaaagtcgtcgtggatgttttcgtaaaggcc  -1564 tctgaaggttttgcagacggttgtcaatgcgttgataaaagtcattccctcgcagatgggggaagaatcagacttggtattgttgttgataaagaagtag  -1464
                                  GATA                                                  GATA
ataatatctctaaactcttctttattgtctaatttcttgaaactacttgaaggaacaggaggagaattttctggaggtaattatgtcattcagaagggcca  -1364
GATA                                                                  repeat sequence 1
attcccttctgtgaaaacgtccagaaatgacatatatggttcaatgttttcaagtacttcttcaagcacctgacggtatcgtggagctgcttcagccat  -1264
                 repeat sequence 2
gttgatgatgtctcacatacgactgttgagtttatccatgcgtacgcccgcttttatacaaagatcccgtgtaagaaactccctccggttcagttcagga  -1164 taggggtgtgtcccagttttacatccaaagttaatatattttttaatataacaaaaaaatcgtaccgcttattggctgctataaaagagggagcacctg  -1064
                                         palindrome
ctcacttggacatcattaaccatcatcaatatggaggagaacatcaatatttgaacctagtcagggagatcctagaagaggagtgaagaaggacgata  -964
                                                                             126 1k-F
gaactggaacaggaactctatccattttggaccccaaatgaggttctctcttcgagacgacactattccagttctcactaccaagaaaattttctggag  -864
                                                                                      repeat sequence 1
aggagttgtggaagaactctcgtggttcatcaggggcaatacagacgccaaagaattggccaagaagaagatacacatctggaacgctaatgggtcgcgg  -764
                                                                 GATA
gaattttttggacagtagagggttatacgatagagcagagggagatttgggacccgtatacggattccaatggcgtcattttggtgctgaatatgatacct  -664
                                                                                              GATA
gttcttccgattatactggaaagggtattgatcaattggccaatatactaaagaccctgagagaaaatccagatgataagaaggatgattatgacggcatg  -564
                                                                     GATA
gaatcctatggatcttcaccttatggctcttcctccatgccacatgactgctcaatttatgtggctaatggagaattgtcgtgccagttgtatcagcga  -464
                                                                        baculovirus early promoter motif
agcggagatgtcgggttgggcgtgcccttcaatattgcatcatactctcttctgactcatctgatggccagtatggtgggtctaaaaccgggagagttta  -364 tcctcactcttggtgacgcacacatttataatacccacattgaggtgttaaagaagcagttgtgccgcgtccctagaccattccctaagttgaggatttt  -264 aatggctccagaaaaattgaggactttactatcgacatgttttatcttgaggggtatcaaccacacagtggaaacttgcagatgaaaatggctgtttga  -164
      repeat sequence 2
atcatgttaaggaatttccttgttactcatttattcctagaaatggtgtaatcgctgttgtgggcggagcatatttgtgtatataagagcccgtgttagc  -64
baculovirus late promoter initiator                      126 R                   TATA box
tcctcgattcagtcacaagagcgcacacacacgcttataactagctctctctctccactcaagatggcctttaattttgaagactctacaaatctctttg  +37
      ↳       direct repeats              direct repeats
transcriptional start site or initiator       translation initiation codon (+1)
```

FIG. 8

SEQUENCE LISTING

```
<160> NUMBER OF SEQ ID NOS: 31

<210> SEQ ID NO 1
<211> LENGTH: 22
<212> TYPE: DNA
<213> ORGANISM: Artificial Sequence
<220> FEATURE:
<223> OTHER INFORMATION: Forward primer for WSSV ORF 126

<400> SEQUENCE: 1
gactctacaa atctctttgc ca                                              22

<210> SEQ ID NO 2
<211> LENGTH: 22
<212> TYPE: DNA
<213> ORGANISM: Artificial Sequence
<220> FEATURE:
```

<223> OTHER INFORMATION: Reverse primer for WSSV ORF 126

<400> SEQUENCE: 2
ctacctttgc accaattgct ag     22

<210> SEQ ID NO 3
<211> LENGTH: 18
<212> TYPE: DNA
<213> ORGANISM: Artificial Sequence
<220> FEATURE:
<223> OTHER INFORMATION: Forward primer for WSSV ORF 242

<400> SEQUENCE: 3
ataccaacaa ccccagaa     18

<210> SEQ ID NO 4
<211> LENGTH: 18
<212> TYPE: DNA
<213> ORGANISM: Artificial Sequence
<220> FEATURE:
<223> OTHER INFORMATION: Reverse primer for WSSV ORF 242

<400> SEQUENCE: 4
atggggcggg atacaaaa     18

<210> SEQ ID NO 5
<211> LENGTH: 20
<212> TYPE: DNA
<213> ORGANISM: Artificial Sequence
<220> FEATURE:
<223> OTHER INFORMATION: Forward primer for WSSV ORF 418

<400> SEQUENCE: 5
gctggaggag gcttgttgat     20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for WSSV ORF 418

<400> SEQUENCE: 6
gggccagaaa tgccttacag     20

<210> SEQ ID NO 7
<211> LENGTH: 20
<212> TYPE: DNA
<213> ORGANISM: Artificial Sequence
<220> FEATURE:
<223> OTHER INFORMATION: Forward primer for WSSV DNA pol gene

<400> SEQUENCE: 7
tgggaagaaa gatgcgagag     20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for WSSV DNA pol gene

<400> SEQUENCE: 8
ccctccgaac aacatctcag     20

```
<210> SEQ ID NO 9
<211> LENGTH: 20
<212> TYPE: DNA
<213> ORGANISM: Artificial Sequence
<220> FEATURE:
<223> OTHER INFORMATION: Forward primer for WSSV VP28 gene

<400> SEQUENCE: 9
ctgctgtgat tgctgtattt                                              20

<210> SEQ ID NO 10
<211> LENGTH: 19
<212> TYPE: DNA
<213> ORGANISM: Artificial Sequence
<220> FEATURE:
<223> OTHER INFORMATION: Reverse primer for WSSV VP28 gene

<400> SEQUENCE: 10
cagtgccaga gtaggtgac                                               19

<210> SEQ ID NO 11
<211> LENGTH: 23
<212> TYPE: DNA
<213> ORGANISM: Artificial Sequence
<220> FEATURE:
<223> OTHER INFORMATION: Forward primer for an intergenic region of WSSV
      genome

<400> SEQUENCE: 11
cagactatta atgtacaagt gcg                                          23

<210> SEQ ID NO 12
<211> LENGTH: 24
<212> TYPE: DNA
<213> ORGANISM: Artificial Sequence
<220> FEATURE:
<223> OTHER INFORMATION: Reverse primer for an intergenic region of WSSV
      genome

<400> SEQUENCE: 12
gaatgattgt tgctggttag aacc                                         24

<210> SEQ ID NO 13
<211> LENGTH: 21
<212> TYPE: DNA
<213> ORGANISM: Artificial Sequence
<220> FEATURE:
<223> OTHER INFORMATION: Forward primer for shrimp beta-actin gene

<400> SEQUENCE: 13
gaygayatgg agaagatctg g                                            21

<210> SEQ ID NO 14
<211> LENGTH: 20
<212> TYPE: DNA
<213> ORGANISM: Artificial Sequence
<220> FEATURE:
<223> OTHER INFORMATION: Reverse primer for shrimp beta-actin gene

<400> SEQUENCE: 14
ccrgggtaca tggtggtrcc                                              20

<210> SEQ ID NO 15
<211> LENGTH: 29
<212> TYPE: DNA
<213> ORGANISM: Artificial Sequence
<220> FEATURE:
```

<223> OTHER INFORMATION: forward primer for cloning the promoter region
      of WSSV ORF 126

<400> SEQUENCE: 15
cggaattcga gatcctagaa agaggagtg                                        29

<210> SEQ ID NO 16
<211> LENGTH: 29
<212> TYPE: DNA
<213> ORGANISM: Artificial Sequence
<220> FEATURE:
<223> OTHER INFORMATION: Reverse  primer for an cloning the promoter
      region of WSSV ORF 126

<400> SEQUENCE: 16
ccgctcgagc ttgagtggag agagagagc                                        29

<210> SEQ ID NO 17
<211> LENGTH: 29
<212> TYPE: DNA
<213> ORGANISM: Artificial Sequence
<220> FEATURE:
<223> OTHER INFORMATION: Forward primer for cloning the promoter region
      of WSSV 126

<400> SEQUENCE: 17
cggaattcga tgatggtgat gtttctagg                                        29

<210> SEQ ID NO 18
<211> LENGTH: 28
<212> TYPE: DNA
<213> ORGANISM: Artificial Sequence
<220> FEATURE:
<223> OTHER INFORMATION: Forward primer for cloning the reverse sequence
      of the 1kb promoter region of WSSV ORF 126

<400> SEQUENCE: 18
cggaattcct tgagtggaga gagagagc                                         28

<210> SEQ ID NO 19
<211> LENGTH: 30
<212> TYPE: DNA
<213> ORGANISM: Artificial Sequence
<220> FEATURE:
<223> OTHER INFORMATION: Reverse primer for cloning the reverse sequence
      of a 1kb promoter region of WSSV ORF 126

<400> SEQUENCE: 19
ccgctcgagg agatcctaga aagaggagtg                                       30

<210> SEQ ID NO 20
<211> LENGTH: 30
<212> TYPE: DNA
<213> ORGANISM: Artificial Sequence
<220> FEATURE:
<223> OTHER INFORMATION: Forward primer for cloning the promoter region
      of WSSV ORF 242

<400> SEQUENCE: 20
ggggtaccgt cttcaacatc ttcttgttcg                                       30

<210> SEQ ID NO 21
<211> LENGTH: 37
<212> TYPE: DNA
<213> ORGANISM: Artificial Sequence
<220> FEATURE:
<223> OTHER INFORMATION: Reverse primer for cloning the promoter region -continued of WSSV ORF 242

<400> SEQUENCE: 21
ataagaatgc ggccgccatg aagatctctg ggaaatg        37

<210> SEQ ID NO 22
<211> LENGTH: 30
<212> TYPE: DNA
<213> ORGANISM: Artificial Sequence
<220> FEATURE:
<223> OTHER INFORMATION: Forward primer for cloning the promoter region
      of WSSV ORF 418

<400> SEQUENCE: 22
cggaattcgt cgcacatgtg tctaaacttc        30

<210> SEQ ID NO 23
<211> LENGTH: 28
<212> TYPE: DNA
<213> ORGANISM: Artificial Sequence
<220> FEATURE:
<223> OTHER INFORMATION: Reverse primer for cloning the promoter region
      of WSSV ORF 418

<400> SEQUENCE: 23
ccgctcgagc aacaagcctc ctccagcc        28

<210> SEQ ID NO 24
<211> LENGTH: 33
<212> TYPE: DNA
<213> ORGANISM: Artificial Sequence
<220> FEATURE:
<223> OTHER INFORMATION: Forward primer for cloning the promoter region
      of WSSV DNA pol gene

<400> SEQUENCE: 24
tagagctcac ttctcctgac actcttgact gat        33

<210> SEQ ID NO 25
<211> LENGTH: 34
<212> TYPE: DNA
<213> ORGANISM: Artificial Sequence
<220> FEATURE:
<223> OTHER INFORMATION: Reverse primer for cloning the promoter region
      of WSSV DNA pol gene

<400> SEQUENCE: 25
gtggaagagg gtgatggagc tggagatgat catc        34

<210> SEQ ID NO 26
<211> LENGTH: 22
<212> TYPE: DNA
<213> ORGANISM: Artificial Sequence
<220> FEATURE:
<223> OTHER INFORMATION: Primer for conducting
      5' RACE of WSSV ORF 126

<400> SEQUENCE: 26
gtacagtact gtccatgtcg at        22

<210> SEQ ID NO 27
<211> LENGTH: 21
<212> TYPE: DNA
<213> ORGANISM: Artificial Sequence
<220> FEATURE:
<223> OTHER INFORMATION: Primer for conducting
      5' RACE of WSSV ORF 126

<400> SEQUENCE: 27
cctcttcatc acctcaatac c					21

<210> SEQ ID NO 28
<211> LENGTH: 24
<212> TYPE: DNA
<213> ORGANISM: Artificial Sequence
<220> FEATURE:
<223> OTHER INFORMATION: Primer for conducting
      3' RACE of WSSV ORF 126

<400> SEQUENCE: 28
gagactgatc gacatggaca gtac					24

<210> SEQ ID NO 29
<211> LENGTH: 2063
<212> TYPE: DNA
<213> ORGANISM: White spot syndrome virus
<220> FEATURE:
<221> NAME/KEY: GATA motif
<222> LOCATION: (120)..(125)
<220> FEATURE:
<221> NAME/KEY: GATA motif
<222> LOCATION: (179)..(184)
<220> FEATURE:
<221> NAME/KEY: GATA motif
<222> LOCATION: (533)..(538)
<220> FEATURE:
<221> NAME/KEY: GATA motif
<222> LOCATION: (587)..(592)
<220> FEATURE:
<221> NAME/KEY: GATA motif
<222> LOCATION: (599)..(604)
<220> FEATURE:
<221> NAME/KEY: Repeat_region
<222> LOCATION: (667)..(673)
<220> FEATURE:
<221> NAME/KEY: Repeat_region
<222> LOCATION: (722)..(728)
<220> FEATURE:
<221> NAME/KEY: Palindrome
<222> LOCATION: (938)..(961)
<220> FEATURE:
<221> NAME/KEY: Repeat_region
<222> LOCATION: (1192)..(1198)
<220> FEATURE:
<221> NAME/KEY: GATA motif
<222> LOCATION: (1269)..(1274)
<220> FEATURE:
<221> NAME/KEY: GATA motif
<222> LOCATION: (1393)..(1398)
<220> FEATURE:
<221> NAME/KEY: GATA motif
<222> LOCATION: (1474)..(1479)
<220> FEATURE:
<221> NAME/KEY: baculovirus early gene promoter motif
<222> LOCATION: (1581)..(1585)
<220> FEATURE:
<221> NAME/KEY: repeat_region
<222> LOCATION: (1808)...(1814)
<220> FEATURE:
<221> NAME/KEY: baculovirus late promoter initiator
<222> LOCATION: (1907)..(1911)
<220> FEATURE:
<221> NAME/KEY: TATA_signal
<222> LOCATION: (1982)...(1986)
<220> FEATURE:
<221> NAME/KEY: transcriptional initiation site
<222> LOCATION: (2010)..(2013)
<220> FEATURE:
<221> NAME/KEY: repeat_region
<222> LOCATION: (2024)...(2031)
<220> FEATURE:
<221> NAME/KEY: repeat_region

<222> LOCATION: (2048)...(2055)

<400> SEQUENCE: 29

| | | | | |
|---|---|---|---|---|
| gatgatggtg | atgtttctag | gcaagaaaaa | ggtctcccga taataaaatt | gccattggat | 60 |
| atcagtcgtt | ttgcctttgt | aacacaagga | gattcgtcca caaatactt | gtatccgaaa | 120 |
| gatatgtcaa | aaggttcaag | tggtgcagat | tttttcattt cagccacgta | atcagaggtg | 180 |
| atattgacga | ttcttgaaaa | gagcctgaat | ctaataacac tcgaacattt | ttcaacgtag | 240 |
| aaaacaatac | cacttcttgc | agaactagta | gacttttca ggctagccaa | acaccgtcc | 300 |
| aacttcttga | tccttctcat | aaccttctct | cttcttcct cagcctgttc | ctttgaagta | 360 |
| aacttgaatc | cagttctgct | gtcatcacca | gtgccaaact tgatgccgtg | cgtctcgcgt | 420 |
| ctcaaaaatc | cattatccat | agagaccaga | agagaatatt ttacgaacaa | aaagtcgtcg | 480 |
| tggatgtttt | cgtaaaggcc | tctgaaggtt | ttgcagacgg ttgtcaatgc | gttgataaaa | 540 |
| gtcattccct | cgcagatggg | ggaagaatca | gacttggtat tgttgttgat | aaagaagtag | 600 |
| ataatatctc | taaactcttc | tttattgtct | aatttcttga aactacttga | aggaacagga | 660 |
| ggagaatttc | tggaggtaat | tatgtcattc | agaagggcca attcccttc | tgtgaaaacg | 720 |
| tccagaaatg | acatatatgg | ttcaatgttt | tcaagtactt cttcaagcac | ctgacggtat | 780 |
| cgtggagctg | cttcagccat | gttgatgatg | tctcacatac gactgttgag | tttatccatg | 840 |
| cgtacgcccg | cttttataca | aagatcccgt | gtaagaaact ccctccggtt | cagttcagga | 900 |
| taggggtgtg | tcccagtttt | acatccaaag | ttaatatatt tttttaatat | aacaaaaaaa | 960 |
| tcgtaccgct | tattggctgc | tataaaagag | ggagcacctg ctcacttgga | catcattaac | 1020 |
| catcatcaat | atggagggag | aacatcaata | tttgaaccta gtcagggaga | tcctagaaag | 1080 |
| aggagtgaag | aaggacgata | gaactggaac | aggaactcta tccattttg | gaccccaaat | 1140 |
| gaggttctct | cttcgagacg | cacactattcc | agttctcact accaagaaaa | ttttctggag | 1200 |
| aggagttgtg | gaagaactct | cgtggttcat | cagggcaat acagacgcca | aagaattggc | 1260 |
| caagaagaag | atacacatct | ggaacgctaa | tgggtcgcgg gaatttttgg | acagtagagg | 1320 |
| gttatacgat | agagcagagg | gagatttggg | accgtatac ggattccaat | ggcgtcattt | 1380 |
| tggtgctgaa | tatgataact | gttcttccga | ttatactgga aagggtattg | atcaattggc | 1440 |
| caatatacta | aagaccctga | gagaaaatcc | agatgataga aggatgatta | tgacggcatg | 1500 |
| gaatcctatg | gatcttcacc | ttatggctct | tcctccatgc cacatgactg | ctcaatttta | 1560 |
| tgtggctaat | ggagaattgt | cgtgccagtt | gtatcagcga agcggagatg | tcgggttggg | 1620 |
| cgtgcccttc | aatattgcat | catactctct | tctgactcat ctgatggcca | gtatggtggg | 1680 |
| tctaaaaccg | ggagagttta | tcctcactct | tggtgacgca cacatttata | atacccacat | 1740 |
| tgaggtgtta | aagaagcagt | tgtgccgcgt | ccctagacca ttccctaagt | tgaggatttt | 1800 |
| aatggctcca | gaaaaaattg | aggactttac | tatcgacatg ttttatcttg | aggggtatca | 1860 |
| accacacagt | ggaaacttgc | agatgaaaat | ggctgtttga atcatgttaa | ggaatttcct | 1920 |
| tgttactcat | ttattcctag | aaatggtgta | atcgctgttg tgggcggagc | atatttgtgt | 1980 |
| atataagagc | ccgtgttagc | tcctcgattc | agtcacaaga gcgcacacac | acgcttataa | 2040 |
| ctagctctct | ctctccactc | aag | | | 2063 |

<210> SEQ ID NO 30
<211> LENGTH: 720
<212> TYPE: DNA
<213> ORGANISM: White spot syndrome virus

```
<220> FEATURE:
<221> NAME/KEY: CDS
<222> LOCATION: (1)...(672)
<220> FEATURE:
<221> NAME/KEY: terminator
<222> LOCATION: (673)...(675)
<220> FEATURE:
<221> NAME/KEY: polyA_signal
<222> LOCATION: (674)...(679)

<400> SEQUENCE: 30 atg gcc ttt aat ttt gaa gac tct aca aat ctc ttt gcc aat atg gac      48
Met Ala Phe Asn Phe Glu Asp Ser Thr Asn Leu Phe Ala Asn Met Asp
 1               5                  10                  15 ttg acg gct ggc aca aca aca gac cct acc cgc ccc aat atc ata ttc      96
Leu Thr Ala Gly Thr Thr Thr Asp Pro Thr Arg Pro Asn Ile Ile Phe
             20                  25                  30 ttt gaa agt cta ctc ccc aac tct ggt att gag gtg atg aag agg cgt     144
Phe Glu Ser Leu Leu Pro Asn Ser Gly Ile Glu Val Met Lys Arg Arg
         35                  40                  45 ctc gta cgg caa gga aag tgt ggg aat ttt gaa gca agt gga ggt gct     192
Leu Val Arg Gln Gly Lys Cys Gly Asn Phe Glu Ala Ser Gly Gly Ala
     50                  55                  60 atg tcg tat ttc tgg ctc gaa gat aat gca gaa gat atg gag aat ctc     240
Met Ser Tyr Phe Trp Leu Glu Asp Asn Ala Glu Asp Met Glu Asn Leu
 65                  70                  75                  80 aac agt ggt tcc cat gtc aag aca aac tgc ttg gca tta ttc ctt caa     288
Asn Ser Gly Ser His Val Lys Thr Asn Cys Leu Ala Leu Phe Leu Gln
                 85                  90                  95 gag ttt atc agc aac tgg att gaa gag act gat cga cat gga cag tac     336
Glu Phe Ile Ser Asn Trp Ile Glu Glu Thr Asp Arg His Gly Gln Tyr
            100                 105                 110 tgt act ttt ccc caa tac atg gac ggt ggg gat ggt tca cgt ggg gga     384
Cys Thr Phe Pro Gln Tyr Met Asp Gly Gly Asp Gly Ser Arg Gly Gly
        115                 120                 125 tat ttt act tcg cta gcc atg aaa tgg atg gct agg gat gtg act ttc     432
Tyr Phe Thr Ser Leu Ala Met Lys Trp Met Ala Arg Asp Val Thr Phe
    130                 135                 140 ttt gtg ttt gtt gat agg aat aat act gta gaa aat gcg gca tcc ata     480
Phe Val Phe Val Asp Arg Asn Asn Thr Val Glu Asn Ala Ala Ser Ile
145                 150                 155                 160 tgg atg tac caa aaa cta cta gca att ggt gca aag gta gta aag gtg     528
Trp Met Tyr Gln Lys Leu Leu Ala Ile Gly Ala Lys Val Val Lys Val
                165                 170                 175 att gtt gac aat gca tca aac cca atg ttt tct gta tgt aat gcg tgt     576
Ile Val Asp Asn Ala Ser Asn Pro Met Phe Ser Val Cys Asn Ala Cys
            180                 185                 190 agg tgc aag tac cca ggc cca gtg tca tac gtt att gaa ggc cat gga     624
Arg Cys Lys Tyr Pro Gly Pro Val Ser Tyr Val Ile Glu Gly His Gly
        195                 200                 205 gtg ggt cat tct gat ttg aca tgt gat gag att tct gga ttc ttt gta     672
Val Gly His Ser Asp Leu Thr Cys Asp Glu Ile Ser Gly Phe Phe Val
    210                 215                 220 taataaaacc ccataagaaa caataatctt ttttattcaa cacccatg                 720

<210> SEQ ID NO 31
<211> LENGTH: 224
<212> TYPE: PRT
<213> ORGANISM: White spot syndrome virus

<400> SEQUENCE: 31

Met Ala Phe Asn Phe Glu Asp Ser Thr Asn Leu Phe Ala Asn Met Asp
```

-continued

```
1               5                   10                  15
Leu Thr Ala Gly Thr Thr Thr Asp Pro Thr Arg Pro Asn Ile Ile Phe
            20                  25                  30

Phe Glu Ser Leu Leu Pro Asn Ser Gly Ile Glu Val Met Lys Arg Arg
            35                  40                  45

Leu Val Arg Gln Gly Lys Cys Gly Asn Phe Glu Ala Ser Gly Gly Ala
            50                  55                  60

Met Ser Tyr Phe Trp Leu Glu Asp Asn Ala Glu Asp Met Glu Asn Leu
65                      70                  75                  80

Asn Ser Gly Ser His Val Lys Thr Asn Cys Leu Ala Leu Phe Leu Gln
                85                  90                  95

Glu Phe Ile Ser Asn Trp Ile Glu Glu Thr Asp Arg His Gly Gln Tyr
                100                 105                 110

Cys Thr Phe Pro Gln Tyr Met Asp Gly Gly Asp Gly Ser Arg Gly Gly
            115                 120                 125

Tyr Phe Thr Ser Leu Ala Met Lys Trp Met Ala Arg Asp Val Thr Phe
            130                 135                 140

Phe Val Phe Val Asp Arg Asn Asn Thr Val Glu Asn Ala Ala Ser Ile
145                 150                 155                 160

Trp Met Tyr Gln Lys Leu Leu Ala Ile Gly Ala Lys Val Val Lys Val
                165                 170                 175

Ile Val Asp Asn Ala Ser Asn Pro Met Phe Ser Val Cys Asn Ala Cys
                180                 185                 190

Arg Cys Lys Tyr Pro Gly Pro Val Ser Tyr Val Ile Glu Gly His Gly
            195                 200                 205

Val Gly His Ser Asp Leu Thr Cys Asp Glu Ile Ser Gly Phe Phe Val
        210                 215                 220
```

PROMOTER SEQUENCES FROM WSSV IMMEDIATE EARLY GENES AND THEIR USES IN RECOMBINANT DNA TECHNIQUES

BACKGROUND OF THE INVENTION

1. Field of the Invention

This invention relates to isolated nucleotide sequences which are derived from a newly identified immediate early gene of white spot syndrome virus (WSSV) and which have promoter activity to drive the transcription of a target gene in a non-native host cell, thus having great potential for use in the field of biotechnology.

2. Description of the Related Art

The production of recombinant polypeptides/proteins is a very important genetic engineering technique in the field of biotechnology. The basic principle involves the cloning of a target gene capable of expressing a desired gene product (e.g., ribozymes and RNA transcripts, industrial and agricultural enzymes, therapeutic proteins, interferons, interleukins, hormones, growth hormones, antigenic polypeptides, antibodies and the like) into a suitable vector, and the subsequent transfer of the resultant recombinant vector into a competent host cell. The thus-formed recombinant host cell can be cultivated in a suitable culture medium under suitable culture conditions, and expression of the target gene can be induced at an opportune time so as to achieve the object of massive production of the desired gene product.

According to current knowledge and techniques in the field of genetic engineering, *Escherichia coli* cells are the most widely used and the most effective host cells, and many types of plasmid vectors for harboring in this bacterial species have been developed. Such plasmid vectors are generally constructed to have an inducible artificial promoter cloned upstream of a target gene, so as to control the expression of said target gene. In general, the most commonly used artificial promoters include lac-trp-tac-trc-araBAD-$\lambda P_R P_L$, and T7 promoters, and these promoters may be induced by the addition of isopropyl-β-D-thiogalactopyranoside (IPTG), lactose, arabinose, a change in temperature or the like (S. C. Makrides et al. (1996), *Microbiol. Rev.,* 60: 512-538).

On the other hand, a cloned target gene can be directly cloned into a vector if it contains a constitutive promoter. When such a target gene is used in the construction of a recombinant vector, it is normally unnecessary to elicit the production of recombinant polypeptides/proteins by induction methods.

Other prokaryotic cells that may be used for conducting vector transformation include, but are not limited to, cells derived from: other species/genera of bacteria (such as *Bacillus subtilis, Serratia marcescens, Lactobacillus* sp., *Streptomyces* sp. and *Salmonella typhi*), *Cyanobacteria, Actinomycetes* and so forth.

However, prokaryotic cells do not, and yeasts only limitedly, carry out post-translational modifications of the expressed polypeptides/proteins, whereas higher eukaryotic cells are able to perform sophisticated protein modifications which are often necessary for the proper function of proteins. Therefore, if post-translational modification(s) is/are needed for recombinant polypeptides/proteins, it may be more desirable to produce the same using eukaryotic cells.

Eukaryotic cells suitable for conducting vector transformation include, for example, fungal cells, protozoan cells, plant cells, insect cells, animal cells, and human cells. Examples of suitable fungal cells are yeast cells, e.g. cells of *Saccharomyces cerevisiae, Pichia pastoris,* and *Kluyveromyces,* such as *K. lactis* and *K. marxianus.* Suitable plant cells are those derived from gynosperms or angiosperms, preferably monocots and dicots, in particular crops, are derived from the roots, shoots, leaves or meristems of these plants, and are cultured in the form of protoplasts or calli. Examples of suitable insect cells are *Drosophila* S2 cells, Sf21 cells and Sf9 cells derived from *Spodoptera frugiperda,* etc. Suitable animal cells may be cultured cells or cells in vivo, preferably derived from vertebrates, and more preferably mammals, and are derived from organs/tissues, such as kidney, liver, lung, ovary, breast, skin, skeleton and blood, of these animals. Representative examples of animal cells include CHO, COS, BHK, HEK-293, HeLa, NIH3T3, VERO, MDCK, MOLT-4, Jurkat, K562, HepG2, etc.

Vectors for use in transforming the above-indicated host cells include those commonly used in genetic engineering technology, e.g. bacteriophages, such as λ phage; plasmids, such as plasmids from *E. coli,* including pBR322, pBR325, pUC12, pUC13, pQE-30, pET12, pET30, etc., plasmids from *Bacillus subtilis,* including pUB110, pTP5, pC194, etc., shuttle vectors for *E. coli* and *Bacillus subtilis,* e.g. pHY300PLK, and plasmids from yeasts, including pSH19, pSH15, etc.; cosmids; viruses, including insect viruses, e.g. baculoviruses, animal viruses, e.g. vaccinia viruses, cytomegalovirus (CMV), retroviruses, etc.

To achieve an efficient expression of a selected target gene, it is desirable to construct a vector containing a functional promoter/regulatory sequence(s) operatively connected to a target gene carried by said vector. Such promoter/regulatory sequence(s) may be derived from any one of the following: viruses, bacterial cells, yeast cells, fungal cells, algal cells, plant cells, insect cells, animal cells, and human cells. For example, a promoter useful in *E. coli* cells includes, but is not limited to, tac promoter, T5 promoter, T7 promoter, T7 A1 promoter, lac promoter, trp promoter, trc promoter, recA promoter, lpp promoter, araBAD promoter, and $\lambda P_R P_L$ promoter. A promoter useful in the cells of *Bacillus* sp. includes, but is not limited to, SPO1 promoter, SPO promoter, penP promoter, etc. A promoter useful in yeast cells includes, but is not limited to, PHO5 promoter, PGK promoter, GAP promoter, ADH promoter, etc. A promoter useful in insect cells includes, but is not limited to, polyhedrin promoter, P10 promoter, OpIE2 (OpMNPV ie2) promoter, etc. A promoter useful in animal cells includes, but is not limited to, SR α promoter, SV40 early promoter, RSV-promoter, HIV-LTR promoter, HSV-TK promoter, CMV promoter, CMV-HSV thymidine kinase promoter, etc. A promoter useful in plant cells includes, e.g., 35S CaMV promoter, actin promoter, ubiquitin promoter, etc. Regulatory elements suitable for use in mammalian cells include CMV-HSV thymidine kinase promoters, SV40 early promoter, RSV-promoters, CMV enhancers and SV40 enhancers.

Further, representative RNA polymerase promoters may be classified into the following types: inducible promoters, constitutive promoters, tissue-specific promoters, and synthetic promoters. Representative inducible promoters are the heat-inducible Hsp70 promoter, a metallothionein promoter, an alcohol dehydrogenase promoter and a galactose promoter; representative constitutive promoters are the Rous sarcoma virus (RSV) LTR promoter, the human cytomegalovirus (CMV) major immediate early gene promoter and the SV40 early promoter; and representative tissue-specific promoters are an alpha globin promoter and a beta globin promoter. Synthetic promoters can be produced by chemically or recombinantly modifying native promoters.

In addition to the lack of post-translational modification machinery, there are other problems associated with expressing some proteins in prokaryotic cells. For example, some expressed heterologous proteins are deposited as insoluble inclusion bodies in prokaryotic cells, making recovery of the proteins difficult. Many of the difficulties associated with prokaryotic expression systems may be overcome by using transformed mammalian cell culture systems to produce post-translationally processed proteins. However, mammalian cell cultures may be relatively inefficient because they grow slowly and are difficult and costly to maintain.

Advances in the culture of insect cells, and the development of baculovirus-based expression systems, have facilitated the expression of heterologous proteins by transformed insect cell lines (Luckow and Summers (1988), *Bio/Tech.*, 6, 47-55; Miller (1988), *Annu. Rev. Microbiol.*, 42, 177-199). To date, the expression of heterologous proteins in transformed insect cell lines has been accomplished primarily using vectors derived from the baculovirus *Autographa californica* multicapsid nucleopolyhedrosis virus (AcMNPV)(Luckow and Summers (1988), supra; Miller (1988), supra).

Baculoviruses are double-stranded DNA viruses that kill infected insect cells by lysis at the end of a typical infection cycle. A variety of baculoviruses are known, each of which is endemic to a particular arthropod species. Baculoviruses are not known to undergo replication in animals outside the Arthropoda.

Gene expression during natural baculovirus infection of an insect is highly regulated and occurs as an ordered cascade. The viral genes may be classified into four different groups according to their place in this cascade of gene expression: immediate early (IE), delayed early (DE), late, and very late. Early gene expression occurs before the onset of viral DNA replication and appears to be essential for the induction of late viral gene expression (Blissard and Rohrmann(1990), *Annu. Rev Entomol.*, 35: 127-155; Guarino and Summers(1988), *J. Virol.*, 62: 463-471; Miller et al.(1983), *Virology*, 126: 376-380). Experimental evidence indicates that baculovirus ie genes are transcribed by host RNA polymerase II in the absence of other viral factors. Baculovirus ie genes are therefore understood to have promoters that are recognized by the host cell transcription machinery.

The above descriptions in connection with baculoviruses and ie genes thereof are excerpted from U.S. 20020116723 A1, which discloses the use of promoters derived from a baculovirus immediate early promoter to control expression of a selectable marker gene that confers resistance to one of the family of bleomycin/phleomycin-type antibiotics. Specifically, it is disclosed in U.S. 20020116723 A1 that ie1 and ie2 promoters derived from the Orgyia pseudotsugata multicapsid nucleopolyhedrosis virus (OpMNPV) ie1 and ie2 genes may be operably linked to a selectable marker gene to control transcription from the selectable marker gene, and that the selectable marker gene may be the Streptoalloteichus hindustanus ble gene which confers Zeocin resistance on insect cells.

Patents and published patent applications describing the construction of virus vectors and/or vectors containing viral promoters include, but are not limited to: U.S. Pat. Nos. 5,077,214; 5,162,222; 5,168,062; 5,385,839; US 20020116723 A1, US 20030108524 A1, US 20030108863A1, US 20030229046 A1, US 20040082531 A1, US 20040161841A1, US 20040197313 A1, WO 99/61636 A1, and WO 0105992 A1.

Literature references relevant to the identification of virus promoters and/or regulatory sequences for constructing vectors useful in the transformation and/or transfection of host cells include, but are not limited to: Tom A. Pfeifer et al. (1997), *Gene*, 788, 183-190; Steven S. Pullen and Paul. D. Friesen, June 1995, 69 (6), 3575-3583; Fan Xiu Zhu et al., *J.* *Virol.*, July 1999, 73 (7), 5556-5567; R. L. Harrison and B. C. Bonning (2003), *J. Gen. Viral.*, 84 (Pt 7), 1827-1842; E. B. Carstens et al., *Virus research* (2002), 83, 13-30; M. K Barnhart et al., *J. Virol.*, January 1997, 71 (1), 337-344; L. A. Guarino and M. D. Summers, *J. Virol.*, February 1986, 57 (2), 563-571; V. A. Olson et al., *J. Virol.*, May 2003, 77 (10), 5668-5677; E. A. van Strien et al., *Arch Virol.* (2000), 145, 2115-2133; V. A. Olson et al., *J. Virol.*, September 2002, 76 (18), 9505-9515; Andrew K Cheung (1999), *Nucleic Acid Research*, 17 (12), 4637-4646; Alejandra Garcia-Maruniak et al., *J, Virol.*, July 2004, 78 (13), 7036-7051; K. Kojima et al. (2001), *Arch Virol.*, 146, 1407-1414.

In spite of the aforesaid, researchers in the art are still endeavoring to explore any potential promoter and/or regulatory sequence that may be used in the construction of recombinant expression vectors useful in the production of recombinant polypeptides/proteins.

White spot syndrome virus (WSSV) or white spot bacilliform virus (WSBV), which is an enveloped, ellipsoid, large, double stranded DNA virus, is one of the most virulent and hazardous viral pathogens of cultivated shrimps worldwide (K. Inouye et al., *Fish Pathol.* (1994), 29:149-158 and *Fish Pathol.* (1996), 31: 39-45; Nakano et al., *Fish Pathol.* (1994), 29 (2):135-139; Takahashi et al., *Fish Pathol.* (1994), 29 (2):121-125; H.-Y. Chou et al. (1995), *Dis. Aquat. Org.*, 23:165-173; J. Huang et al., *Marine Fish Res.* (1995), 16:1-10 and *Marine Fish Res.* (1995), 16:11-23; C.-F. Lo, et al., *Dis. Aquat. Org.* (1996), 27, 215-225 and *J. Fish. Soc.* Taiwan (2003), 30, 1-13; C.-H. Wang et al. (1995), *Dis Aquat. Org.*, 23: 239-242, C. Wongteerasupaya et al. (1995), *Dis. Aquat. Org.*, 21: 69-77; T. W. Flegel (1997), *World J. Microbiol. Biotech.*, 13, 433-442; Y. Lu et al. (1997), *J. Gen. Virol.*, 84:1517-1523). It also attacks many other crustaceans such as crabs and crayfishes. In addition, due to the uniqueness of WSSV, it is difficult to interpret the infection strategy of WSSV by directly applying the infection models of other viruses. As a consequence, the infection strategy of WSSV may need to be investigated ab initio.

Morphologically, the virion of WSSV is a nonoccluded, enveloped particle of approximately 275 by 120 nm with an olive-to-bacilliform shape, and has a nucleocapsid (300 by 70 nm) with periodic striations perpendicular to the long axis (C.-H. Wang et al. (1995), *Dis Aquat. Org.*, 23: 239-242; C. Wongteerasupaya et al. (1995), *Dis. Aquat. Org.*, 21: 69-77). The most prominent feature of WSSV is the presence of a tail-like extension at one end of the virion (Wongteerasupaya et al. (1995), supra; S. Durand et al. (1997), *Dis. Aquat. Org.*, 29:205-211).

Complete genome sequencing has been performed on three WSSV isolates (for Taiwan isolate WSSV T-1, see NCBI Accession No. AF440570; for Thailand isolate, see NCBI Accession No. AF369029; and for China isolate, see NCBI Accession No. AF332093). The WSSV genome (~300 kb) is ~30 kb smaller than the 335,593 bp genome of the Ectocarpus siliculosus virus (EsV-1; family Phycodnaviridae), which is the largest virus genome sequenced to date (J. L. van Etten et al. (2002), *Arch Virol.*, 147, 1479-516).

Previous studies on individual genes and analyses of the complete genome sequence suggest that WSSV does not belong to any known virus family (M.-F. Tsai et al., *Virology* (2000), 277, 92-99 and *Virology* (2000), 277:100-110; W. J. Liu et al., (2001), *Virology* 289: 362-377; Feng Yang et al., *J. Virol.*, December 2001, 75 (23): 11811-11820; C. W. Mariëlle et al., *Virology*. Jul. 20, 2001, 286 (1):7-22; L.-L. Chen et al. (2002), *Virology* 301: 136-147; H. Marks et al. (2003), *J Gen Virol* 84:1517-1523). Recently, WSSV has been proposed as the type species of the genus Whispovirus, family Nimaviridae (M. A. Mayo (2002), *Arch. Virol.*, 147, 1655-1663).

In the Applicants' earlier genomic analysis directed to the Taiwan isolate using microarray technique, this isolate was identified to have a total of 532 putative open reading frames (ORFs) that start with an ATG initiation codon and probably encodes a polypeptide of at least 60 amino acids long, amongst which, 39 ORFs have so far been identified as WSSV structural genes and less than a dozen as non-structural genes. In addition, transcripts have been detected for ~90% of these ORFs (H.-C. Wang, et al. "*DNA microarrays of the white spot syndrome virus genome: genes expressed in the gills of infected shrimp,*" *Marine Biotechnology*, in press). In addition, most of the ORFs posted for the Taiwan isolate show no significant similarity to other known proteins based on homology searches against the NCBInr database. Similar results have been reported for the other two isolates (Mariëlle C. W. van Hulten et al., *Virology*. Jul. 20, 2001, 286 (1):7-22; Feng Yang et al., *J. Virol.*, December 2001, 75 (23): 11811-11820).

However, although the temporal expression of WSSV genes has been investigated both by individual gene studies (L.-L. Chen et al. (2002), *Virology*, 301, 136-147; J.-H. Leu, et al. (2005), *J. Virol.*, January 2005, 79 (1), 140-149, W.-J. Liu, et al. (2001), *Virology* 289, 362-377; M.-F. Tsai et al., *Virology* (2000), 277, 92-99 and *Virology* 277 (2000), 100-110) and by global analysis (M.-F. Tsai et al. (2004), *J. Virol.* 78, 11360-11370; H.-C. Wang et al., "*DNA microarrays of the white spot syndrome virus genome: genes expressed in the gills of infected shrimp,*" *Marine Biotechnology*, in press), heretofore, no WSSV immediate early (IE) gene has been identified.

As noted from literature, the expression of viral IE genes depends on the host cell machinery and occurs independently of any viral de novo protein synthesis, which means that the IE genes are especially important in determining host range (P. D. Friesen (1997), "*Regulation of Baculovirus early gene expression,* " In: Miller, L. K., (Ed.), The baculoviruses. Plenum Press, New York and London, pp. 141-170). The IE gene products, once expressed, may function as regulatory trans-acting factors and may serve to initiate viral replicative events during infection. In the cascade of viral regulatory events, successive stages of virus replication are dependent on the proper expression of the genes in the preceding stage. For example, during infection by the large DNA viruses, such as baculoviruses and herpesviruses, gene expression is regulated such that the immediate early (IE or α) genes are transcribed first, followed by the expression of the early (E or β) and late (L or γ) genes, respectively (G. W. Blissard (1996), *Cytotechnology*, 20, 73-93, G. W. Blissard and G. F. Rohrmann (1990), *Annu. Rev. Entomol.*, 35, 127-155; P. D. Friesen and L. K Miller (1986), *Curr. Top. Microbiol. Immunol.* 131, 31-49; R. W. Honess and B. Roizman (1974), *J. Virol.*, 14, 8-19).

To study the transcription of viral IE genes, viral infection is induced in the presence of a protein synthesis inhibitor, usually cycloheximide (CHX), which prevents de novo protein synthesis by preventing translation. In case that translation (but not transcription) of the IE genes is impeded, the viral infection cycle will likewise be blocked at the IE stage. Therefore, the detected presence of RNA transcript during viral infection in the constant presence of CHX is good evidence for the identification of viral IE genes.

Here for the first time, in spite of the lack of any well-acknowledged immortalized shrimp cell line and the difficulty of using CHX in vivo, the Applicants successfully used CHX as an inhibitor to block de nova viral protein synthesis. A global analysis microarray technique and RT-PCR was subsequently used to determine the transcription pattern of WSSV, from the results of which 3 candidate WSSV immediate early (ie) genes were identified and were designated as ie1, ie2 and ie3. In addition, promoter-regulatory regions cloned from the WSSV ie1 gene were proven to have promoter activity in non-native host cells, i.e. Sf9 insect cells, thus having great potential for use in the field of recombinant DNA technology.

SUMMARY OF THE INVENTION

Therefore, according to a first aspect, this invention provides an isolated WSSV immediate early promoter-regulatory region consisting essentially of a nucleotide sequence selected from the group consisting of:
  (i) a nucleotide sequence of SEQ ID NO:29;
  (ii) a 5'-truncated fragment of the nucleotide sequence of
     (i) which has at least 92 nucleotide residues as calculated from the 3' end of SEQ ID NO:29;
  (iii) a nucleic acid sequence which is amplified from polymerase chain reaction using a WSSV genomic DNA as template and a primer pair having a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16;
  (iv) a nucleic acid analogue of the nucleotide sequence of (i), which has at least about 60% sequence identity to the nucleotide sequence of (i) and which can drive the expression of a target gene operatively connected thereto;
  (v) a nucleic acid analogue of the 5'-truncated fragment of (ii), which has at least about 60% sequence identity to the 5'-truncated fragment of (ii) and which can drive the expression of a target gene operatively connected thereto;
  (vi) a variant of the nucleotide sequence of (i), which contains at least one conservative substitution and which can drive the expression of a target gene operatively connected thereto; and
  (vii) a variant of the 5'-truncated fragment of (ii), which contains at least one conservative substitution and which can drive the expression of a target gene operatively connected thereto.

The aforesaid WSSV immediate early promoter-regulatory region is capable of triggering the expression of a heterologus gene in non-native host cells and, thus, can be used in the construction of a variety of recombinant expression vectors for transforming a broad spectrum of host cells. Therefore, according to a second aspect, this invention provides recombinant expression vectors, which are constructed to comprise a target gene encoding a selected gene product, and the aforesaid WSSV immediate early promoter-regulatory region operatively connected to the target gene.

According to a third aspect, this invention provides recombinant host cells produced from the transformation of host cells with the aforesaid recombinant expression vector.

It is contemplated that the practice of this invention is not limited to the use of specific host cells. In fact, this invention can be applied to a diversity of prokaryotic and eukaryotic host cells, including bacterial cells, yeast cells, fungal cells, plant cells, insect cells, mammalian cells, etc., and can be used to produce useful ribozymes and RNA transcripts, and different kinds of proteins, including proteins present in cytoplasms or periplasmic spaces, proteins present on cell membranes or extracellular proteins, and enzymes available for use in industry and in agriculture, food industry, environmental industry, aquaculture and animal husbandry, particularly pharmaceutical proteins and peptides, such as interferons, human and animal hormones, immunogenic antigens, and antibodies.

According to a fourth aspect, this invention provides a primer pair for the cloning of a WSSV immediate early promoter-regulatory region, comprising a forward primer and a reverse primer, the forward primer consisting essentially of a nucleotide sequence selected from nucleotide sequences as shown in SEQ ID NO:15 (i.e. primer 126-1k-F shown in Table 2 described in the Examples) and SEQ ID NO:17 (i.e. primer 126-2k-F shown in Table 2 described in the Examples), the reverse primer consisting essentially of a nucleotide sequence of SEQ ID NO:16 (i.e. primer 126-R shown in Table 2 described in the Examples).

BRIEF DESCRIPTION OF THE DRAWINGS

Other features and advantages of the present invention will become apparent in the following detailed description of the preferred embodiment with reference to the accompanying drawings, of which:

FIG. 5 shows the mapping of 5' and 3' ends of the WSSV ie1 transcripts, in which the primers used for 5' RACE and 3' RACE (126SP1, 126SP2, 126SP3 and 128SP1) are underlined; the shaded region between −92 and −43 nt in front of the translation start indicates the potential basal promoter element as predicted by the NNPP program; the bent arrows indicate the transcriptional start sites as revealed by sequencing seven randomly chosen 5' RACE clones; the TATA and polyadenylation signal (AATAAA) are boxed and boldfaced, respectively; and the poly(A) addition site is indicated by an arrow;

FIG. 6 shows the 5' UTRs of the WSSV DNA polymerase, RR1, RR2 and IE1 genes, in which the Initiation start sites are all located ~26 nt downstream of the TATA box; the TATA boxes are shaded; and the transcription start sites identified by 5' RACE are indicated with bent arrows;

FIG. 8 shows the DNA sequence organization and location of predicted regulatory motifs within the 2 kbp WSSV ie1 promoter/enhancer region.

DETAILED DESCRIPTION OF THE INVENTION

Figure 1:
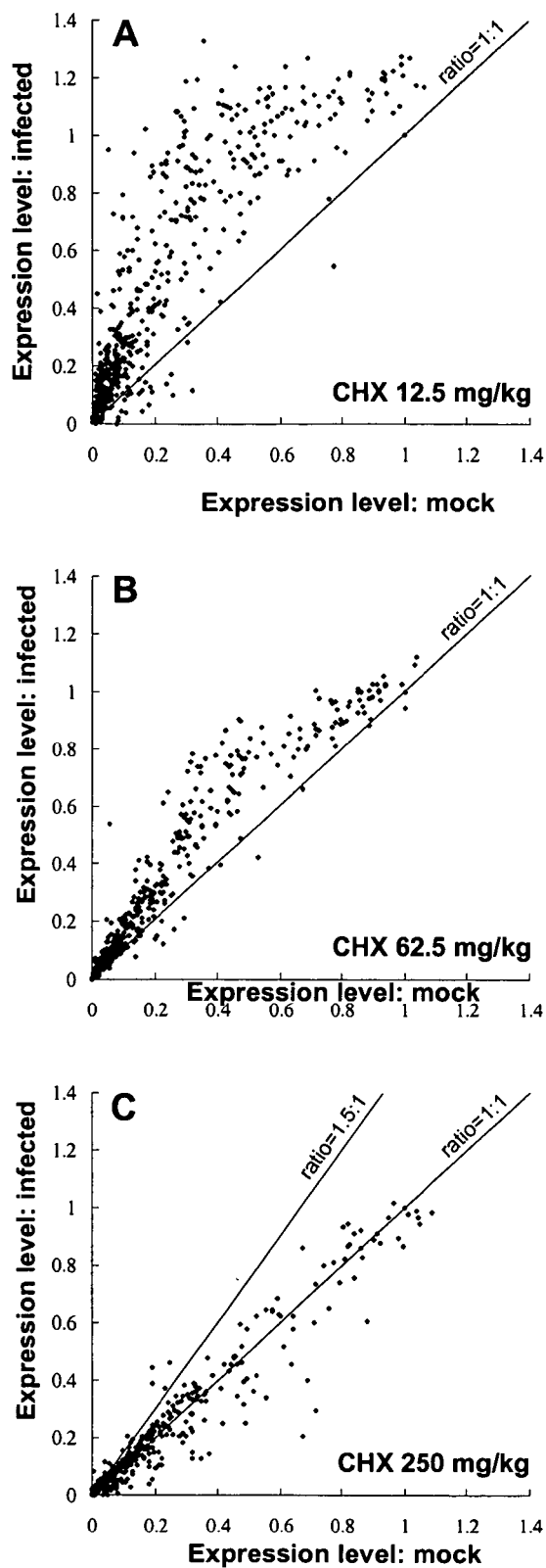
FIG. 1 shows the scatterplots of normalized Cy3 florescence intensities (i.e. expression levels) for the 532 WSSV ORFs on the microarrays under conditions of WSSV infection (vertical axis) versus mock infection (horizontal axis) in three virus challenge trials with different doses of CHX, in which panel A: 12.5 mg/kg CHX treatment; panel B: 62.5 mg/kg CHX treatment; and panel C: 250 mg/kg CHX treatment.

Unless defined otherwise, all technical and scientific terms used herein have the meaning commonly understood by a person skilled in the art to which this invention belongs. For clarity, the following definitions are used herein.

The term "promoter sequence" as used herein refers to a DNA sequence, which is generally located upstream of a gene present in a DNA polymer, and which provides a site for initiation of the transcription of said gene into mRNA. Promoter sequences suitable for use in this invention may be derived from viruses, bacteriophages, prokaryotic cells or eukaryotic cells, and may be a constitutive promoter or an inducible promoter.

A promoter is isolated when it is not immediately contiguous with (i.e., covalently linked to) the coding sequences with which it is normally contiguous in the naturally occurring genome of the organism from which it is derived. By isolated, it is meant that an isolated substance has been substantially separated or purified from other components, such as biological components, with which it would otherwise be associated, for example in vivo, so that the isolated substance may itself be manipulated or processed. The term "isolated" therefore includes substances purified by standard purification methods, substances prepared by recombinant DNA technology in a host, and chemically synthesized substances. Accordingly, it is contemplated that the isolated WSSV immediate early promoter-regulatory region according to this invention may be obtained by isolation from natural sources, chemical synthesis, and recombinant DNA technology.

Transcriptional and translational control sequences are DNA regulatory sequences, such as promoters, enhancers, polyadenylation signals, terminators and the like, that provide for the expression of a coding sequence in a host cell. A "cis-element" is a nucleotide sequence that interacts with protein(s) which can upregulate or downregulate expression of a specific gene locus.

Certain DNA sequences which usually precede a gene in a DNA polymer and which provide a site for initiation of the transcription of that gene into mRNA are referred to as "promoter" sequences. Other DNA or RNA sequences, usually but not necessarily "upstream" of a structural gene, bind proteins that determine the frequency or rate of transcription and/or translation initiation. These other sequences, including attenuators, enhancers, operators and the like, are referred to as "regulator" sequences. Thus, sequences which operate to determine whether the transcription and eventual expression of a gene will take place are collectively referred to as "promoter/regulator" DNA sequences.

A DNA "coding sequence" is a double-stranded DNA sequence which is transcribed into RNA, and the RNA is translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, sequences from the genomes of viruses that infect prokaryotes or eukaryotes, cDNA from eukaryotic mRNA, genomic DNA sequences from eukaryotic (e.g., mammalian) DNA, and even synthetic DNA sequences. A polyadenylation signal and transcription termination sequence are usually located downstream of the coding sequence. A "cDNA" is defined as copy-DNA or complementary-DNA, and is a product of a reverse transcription reaction from a mRNA transcript.

A "signal sequence" can also be included within the coding sequence, and encodes a signal peptide, N-terminal to the polypeptide, that communicates to the host cell and directs the polypeptide to the appropriate cellular location. Signal sequences can be found associated with a variety of proteins native to prokaryotes and eukaryotes.

The terms "nucleic acid" and "nucleic acid sequence" as used herein refer to a deoxyribonucleotide or ribonucleotide sequence in single-stranded or double-stranded form, that comprise naturally occurring and known nucleotides or artificial chemical mimics. The term "nucleic acid" as used herein is interchangeable with the terms "gene," "cDNA," "mRNA," "oligo-nucleotide" and "polynucleotide" in use.

Unless otherwise indicated, a nucleic acid sequence, in addition to the specific sequences described herein, also covers its complementary sequence, and the conservative analogues, related naturally occurring structural variants and/or synthetic non-naturally occurring analogs thereof. Specifically, constitutive substitutions may be produced by, for instance, a nucleotide residue substitution at a nucleotide residue of the specific sequences described herein without affecting the promoter activity thereof.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing," "molecular cloning" and "genetic engineering." The product of these manipulations results in a "recombinant" or "recombinant molecule."

Techniques for manipulating nucleic acids, such as those for generating mutation in sequences, subcloning, labeling, probing, sequencing, hybridization and so forth, are described in detail in scientific publications and patent documents. See, for example, Sambrook J, Russell D W (2001) Molecular Cloning: a Laboratory Manual, 3rd ed. Cold Spring Harbor Laboratory Press, New York; Current Protocols in Molecular Biology, Ausubel ed., John Wiley & Sons, Inc., New York (1997); Laboratory Techniques in Biochemistry and Molecular Biology: Hybridization With Nucleic Acid Probes, Part I, Theory and Nucleic Acid Preparation, Tijssen ed., Elsevier, N.Y. (1993).

The sequence identity of two polynucleotides may be determined by several different methods known to persons skilled in the art including, but not limited to, BLAST program of Altschul et al. (*J. Mol. Biol.*, 215, 403-410, 1990).

For the purposes of defining this invention, a promoter region is bounded at its 3' terminus by the transcription initiation site, and extends upstream (5' direction on the non-transcribed strand) to include the minimum number of nucleotides necessary to initiate transcription at levels detectable above background. Additionally, the sequence of a promoter region may extend upstream (5' direction on the non-transcribed strand) to include all nucleotides that affect, either qualitatively or quantitatively, the operation and/or efficiency of the promoter region. Within the sequence of the promoter region will be found a transcription initiation site, as well as protein binding domains responsible for the binding of RNA polymerase. Eukaryotic promoters often, but not always, contain "TATA" boxes and "CAT" boxes.

The term "operatively connected" as used herein means that a first sequence is disposed sufficiently close to a second sequence such that the first sequence can influence the second sequence or regions under the control of the second sequence. For instance, a promoter sequence may be operatively connected to a gene sequence, and is normally located at the 5'-terminus of the gene sequence such that the expression of the gene sequence is under the control of the promoter sequence. In addition, a regulatory sequence may be operatively connected to a promoter sequence so as to enhance the ability of the promoter sequence in promoting transcription. In such case, the regulatory sequence is generally located at the 5'-terminus of the promoter sequence.

The term "expression vector" as used herein refers to any recombinant expression system capable of expressing a selected nucleic acid sequence, in any host cell in vitro or in vivo, constitutively or inducibly. The expression vector may be an expression system in linear or circular form, and covers expression systems that remain episomal or that integrate into the host cell genome. The expression system may or may not have the ability to self-replicate, and it may drive only transient expression in a host cell, According to this invention, the term "transformation" can be used interchangeably with the term "transfection" when such term is used to refer to the introduction of an exogenous nucleic acid molecule into a selected host cell. According to techniques known in the art, a nucleic acid molecule (e.g., a recombinant DNA construct or a recombinant vector) can be introduced into a selected host cell by various techniques, such as calcium phosphate- or calcium chloride-mediated transfection, electroporation, microinjection, particle bombardment, liposome-mediated transfection, transfection using bacteriaphages, transduction using retroviruses or other viruses (such as vaccinia virus or baculovirus of insect cells), protoplast fusion, *Agrobacterium*-mediated transformation, or other methods.

The terms "cell," "host cell," "transformed host cell" and "recombinant host cell" as used herein can be interchangeably used, and not only refer to specific individual cells but also include sub-cultured offsprings or potential offsprings thereof. Sub-cultured offsprings formed in subsequent generations may include specific genetic modifications due to mutation or environmental influences and, therefore, may factually not be fully identical to the parent cells from which the sub-cultured offsprings were derived. However, sub-cultured cells still fall within the coverage of the terms used herein.

The terms "polypeptide," "peptide" and "protein" as used herein can be interchangeably used, and refer to a polymer formed of amino acid residues, wherein one or more amino acid residues are naturally occurring amino acids or artificial chemical mimics.

In the Applicants' earlier investigation, a viral isolate of WSSV, i.e. the *Penaeus monodon* WSSV 1994 Taiwan isolate (WSSV T-1), which was isolated from *Penaeus monodon*, was deposited in the China Center for Type Culture Collection (CCTCC, Wuhan University, Luo Jia Shan, Wuhan, Hubei, 430072, People's Republic of China) under the Budapest Treaty on Jan. 11, 1996 and was given accession number CCTCC-V96001 (see U.S. Pat. Nos. 5,824,535 and 6,190,862 issued to Guang-Hsiung Kou et al and L.-L. Chen et al. (2002), *Virology* 301, 136-147). The complete genome of this Taiwan isolate was subsequently sequenced and was deposited in the NCBI database under Accession No. AF440570 via direct submission.

To the Applicants' knowledge, heretofore, no WSSV immediate early (IE) gene has been identified in any report. In this invention, the Applicants used cycloheximide (CHX) as an inhibitor to block de novo viral protein synthesis in WSSV-infected shrimps, followed by examining the RNA transcripts of viral immediate early genes by WSSV DNA (ORF/gene) microarrays designed based on WSSV PCR products using specific primers derived from the 532 ORFs of WSSV T-1 (see Table 1 described in the following Examples). Three ORFs, i.e. ORF126, ORF242 and ORF418, that may be candidates of WSSV immediate early genes, were successfully identified. A genomic sequence comparison of three WSSV isolates reported so far reveals that no deletion of any one of these three ORFs occurs in the three known WSSV isolates. ORF126, ORF242 and ORF418 were therefore designated as WSSV ie1 (immediate early gene #1), ie2 and ie3, respectively.

A transient reporter assay was subsequently performed to explore the potential of the promoter regions of these three WSSV IE gene candidates in triggering the expression of a heterologous gene, e.g. EGFP (enhanced green fluorescence protein) gene, which also acts as a reporter gene in the assay, in a non-native host cell, e.g. Sf9 insect cells. The primers used for the construction of transient expression vectors are listed in Table-2 described in the Examples. Surprisingly, the cloned 1 kbp and 2 kbp promoter regions of WSSV ie1 according to this invention were functional in non-native host cells of WSSV, suggesting that the promoter region of WSSV ie1 has great potential for use in the construction of a variety of recombinant expression vectors for transforming a broad spectrum of host cells.

WSSV ie1 was further subjected to 5'/3' RACE analyses using primers listed in Table 3 described in the following Examples. The obtained results reveal that the −52 nt G relative to the ATG translational start represents the major transcriptional start point of WSSV ie1. In addition, a putative TATA box (TATAA) was found upstream (−26 nt) of the transcriptional initiation site (at −82 nt to −78 nt relative to the ATG translational start). The TATA motif and the transcription initiator together are considered to be the basal elements of the RNA polymerase II promoter. NNPP (Neural Network for promoter prediction) analysis of upstream sequences of the WSSV ie1 putative transcription start site identified a high-probability predicted basal promoter region between −92 nt and −43 nt in front of the putative translation start codon. In addition, the experimental results obtained from the promoter activity assay suggest that the transcription of WSSV ie1 may not be limited to its native host RNA polymerase II.

In addition, according to nucleotide sequence analysis, the 5' UTR (untranslated region) of WSSV ie1, was found to include several sequences that match the consensus sequences of the GATA motif (A/T)GATA(G/A). This is potentially important because the GATA motif is recognized as a binding site for transcription factors, for example in the promoter of the baculovirus OpMNPV IE gene, gp64 (P. H. Kogan and G. W. Blissard (1994), *J. Virol.*, 68, 813-822). There also exist several other possible regulatory elements, including two direct repeat sequences (CACACACA (positions 2024-2030 of SEQ ID NO:29) and CTCTCTCTCT (positions 2045-2054 of SEQ ID NO:29)), the repetition of two short sequences (TTTCTGG and CCAGAAA), the baculovirus early gene promoter motif (upstream regulatory element) (CGTGC)(R. L. Harrison and B. C. Bonning (2003), *J. Gen. Virol.*, 84 (Pt 7), 1827-1842), the baculovirus late promoter initiator (TTAAG)(L. A. Guarino and M. W. Smith (1990), *Virology*, 179, 1-8; T. D. Morris and L. K. Miller (1994), *Gene*, 140, 147-153), and a palindromic sequence that may function as a transcriptional enhancer (C. T. McMurray et al. (1991), *Proc. Natl. Acad. Sci. USA.*, 88, 666-670, C. Rasmussen et al. (1996), *Virology*, 224, 235-245).

Figures 5, 6:
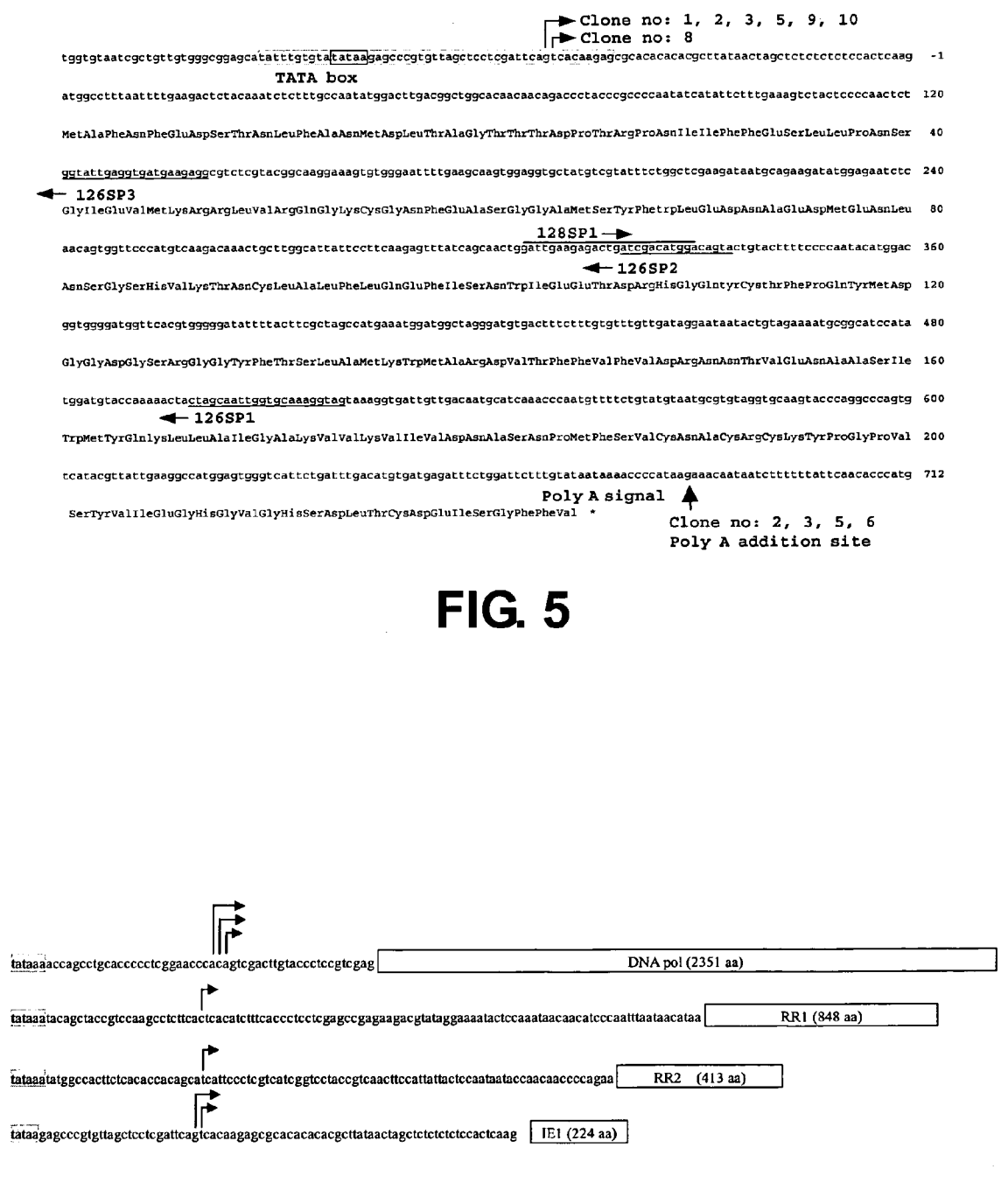

In addition to the aforesaid, sequence analysis of the cloned 3' RACE products revealed that poly (A) was added at a site 17 nt downstream of the AATAAA polyadenylation signal (see FIG. 5).

BLAST analysis of the GenBank/EMBL, SWISSPROT and PIR databases predicted that the WSSV ie1 coding region contains the Cys2/His2-type zinc finger motif. This motif has a role in DNA binding, and its presence implies that WSSV ie1 may function as a transcription factor.

The nucleotide sequence of the cloned 2 kbp promoter region of WSSV ie1, which was amplified by PCR using primer 126-2k-F (SEQ ID NO:17) and primer 126-R (SEQ ID NO:16), is shown in SEQ ID NO:29. The nucleotide sequence of the WSSV ie1 coding region and a putative amino acid sequence encoded thereby are shown in SEQ ID NO:30 and SEQ ID NO:31 respectively.

Based on the aforesaid, this invention provides an isolated WSSV immediate early promoter-regulatory region consisting essentially of a nucleotide sequence selected from the group consisting of:

(i) a nucleotide sequence of SEQ ID NO:29;

(ii) a 5'-truncated fragment of the nucleotide sequence of (i) which has at least 92 nucleotide residues as calculated from the 3' end of SEQ ID NO:29;

(iii) a nucleic acid sequence which is amplified from polymerase chain reaction using a WSSV genomic DNA as template and a primer pair having a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16;

(iv) a nucleic acid analogue of the nucleotide sequence of (i), which has at least about 60% sequence identity to the nucleotide sequence of (i) and which can drive the expression of a target gene operatively connected thereto;

(v) a nucleic acid analogue of the 5'-truncated fragment of (ii), which has at least about 60% sequence identity to the 5'-truncated fragment of (ii) and which can drive the expression of a target gene operatively connected thereto;

(vi) a variant of the nucleotide sequence of (i), which contains at least one conservative substitution and which can drive the expression of a target gene operatively connected thereto; and (vii) a variant of the 5'-truncated fragment of (ii), which contains at least one conservative substitution and which can drive the expression of a target gene operatively connected thereto.

According to this invention, when the isolated WSSV immediate early promoter-regulatory region consists essentially of a 5'-truncated fragment of the nucleotide sequence (i), it preferably has at least 160 nucleotide residues as calculated from the 3' end of SEQ ID NO:29. More preferably, the 5'-truncated fragment of the nucleotide sequence (i) has at least 250 nucleotide residues as calculated from the 3' end of SEQ ID NO:29. More preferably, the 5'-truncated fragment of the nucleotide sequence (i) has at least 500 nucleotide residues as calculated from the 3' end of SEQ ID NO:29. Most preferably, the 5'-truncated fragment of the nucleotide sequence (i) has at least 1000 nucleotide residues as calculated from the 3' end of SEQ ID NO:29.

The isolated WSSV immediate early promoter-regulatory region according to this invention may be obtained by PCR amplification using the genomic DNA of the Taiwan, Thailand or China isolate of WSSV, and a primer pair having a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16. In a preferred embodiment of this invention, the DNA template is extracted from the Taiwan isolate WSSV T-1, samples of which were deposited in the China Center for Type Culture Collection under an accession number CCTCC-V96001.

The isolated WSSV immediate early promoter-regulatory region according to this invention may also comprise conservative variants and synthetic analogues (such as deletions, insertions, inversion, substitutions or addition of sequences) of the nucleotide sequence of SEQ ID NO:29, provided that such variants and analogues can likewise trigger the transcription of downstream located and operatively connected sequences.

In various embodiments, such variants and analogues may be substantially homologous as that term is used above, or greater than 60%, 70% to 100%, at least 80%, at least 90% or at least 95% identical as determined using algorithms described above.

The isolated WSSV immediate early promoter-regulatory region according to this invention may be carried in an expression cassette. As used herein, the term "expression cassette" refers to a synthetically or recombinantly produced nucleic acid construct that carries a series of nucleic acid elements to permit the transcription and translation of a specific nucleic acid in a target cell. A variety of strategies are available for combing or ligating fragments of DNA, and depending on the nature of the termini of the DNA fragments, a suitable strategy will be readily apparent to persons skilled in the art.

The aforesaid WSSV immediate early promoter-regulatory region is capable of driving the expression of a heterologus gene in non-native insect host cells and, thus, can be used in the construction of a variety of recombinant expression vectors for transforming a broad spectrum of host cells.

Therefore, this invention also provides recombinant expression vectors, which are constructed to comprise a first target gene encoding a first gene product, and the aforesaid isolated WSSV immediate early promoter-regulatory region operatively connected to the first target gene.

Preferably, the isolated WSSV immediate early promoter-regulatory region is located upstream of the first target gene in forward orientation.

The construction of such vectors by standard techniques is well known to one of ordinary skill in the art. Vectors suitable for use in this invention include those commonly used in genetic engineering technology, such as bacteriophages, plasmids, cosmids, viruses, or retroviruses.

Vectors suitable for use in this invention may include other expression control elements, such as a further promoter sequence located apart from the WSSV immediate early promoter-regulatory region, a second target gene encoding a second gene product, a transcription starting site, a transcription termination site, a ribosome binding site, a secretion signal coding sequence, a RNA splicing site, a Shine-Dalgam sequence, a marker gene, a reporter gene, an antibiotic-resistance gene, a translation termination site, an insertion cloning location, an enhancer sequence, a polyadenylation site, a regulatory sequence, etc. In addition, the vectors of the present invention may comprise a sequence of nucleotides for one or more restriction endonuclease recognition sites. These sequences are well known to those skilled in the art.

Marker genes suitable for use in this invention include, for instance, dihydrofolate reductase gene and G418 or neomycin resistance gene useful in eukaryotic cell cultures, Zeocin resistance gene useful in insect cell cultures, and ampicillin, streptomycin, tetracycline or kanamycin resistance gene useful in *E. Coli* and other bacterial cultures.

In a preferred embodiment of this invention, the recombinant expression vector further comprises a second target gene located downstream of and operatively connected to a further promoter sequence which may be or may not be a WSSV immediate early promoter-regulatory region as disclosed herein.

According to this invention, the first and second target genes independently encode a gene product selected from the group consisting of enzymes, therapeutic polypeptides, antigenic determinants and antibodies.

In a preferred embodiment of this invention, the recombinant expression vector is pIZΔIE/WSSV126-2k/V5-EGFP-His.

In another preferred embodiment of this invention, the recombinant expression vector is pIZΔIE/WSSV126-1k/V5-EGFP-His.

The aforesaid recombinant expression vectors can be used to transform or transfect an intended host cell. Therefore, this invention provides recombinant host cells produced from the transformation of host cells with the aforesaid recombinant expression vector.

It is contemplated that the practice of this invention is not limited to the use of specific host cells. In fact, this invention can be applied to a diversity of prokaryotic and eukaryotic host cells, including bacterial cells, yeast cells, fungal cells, plant cells, insect cells, mammalian cells, etc., and can be used to produce useful ribozymes and RNA transcripts, and different kinds of proteins, including proteins present in cytoplasms or periplasmic spaces, proteins present on cell membranes or extracellular proteins, and enzymes available for use in industry and in agriculture, food industry, environmental industry, aquaculture and animal husbandry, particularly pharmaceutical proteins and peptides, such as interferons, human and animal hormones, immunogenic antigens, and antibodies.

Host cells that may be used in this invention may be prokaryotic or eukaryotic cells, and may be non-transformed/transfected cells, or cells transformed/transfected with at least one recombinant nucleic acid sequence other than the specific nucleic acid sequences described herein.

Prokaryotic cells suitable for use in this invention include, but are not limited to, cells derived from: bacteria, e.g., *E. coil, Bacillus subtilis, Lactobacillus* sp., *Streptomyces* sp., and *Salmonella typhi; Cyanobacteria; Actinomycetes,* etc.

Eukaryotic cells suitable for use in this invention include, for example, fungal cells, protozoan cells, plant cells, insect cells, animal cells, and human cells. Examples of suitable fungal cells are yeast cells, such as cells of *Saccharomyces cerevisiae* or *Pichia pastoris*. Suitable plant cells are those derived from gynosperms or angiosperms, preferably monocots and dicots, in particular crops, are derived from the roots, shoots, leaves or meristems of these plants, and are cultured in the form of protoplasts or calli. Examples of suitable insect cells are *Drosophila* S2 cells, and Sf21 cells and Sf9 cells derived from *Spodoptera frugiperda*. Suitable animal cells may be cultured cells or cells in vivo, preferably derived from vertebrates, and more preferably mammals, and are derived from organs/tissues, such as kidney, liver, lung, ovary, breast, skin, skeleton and blood, of these animals. Representative examples of animal cells include CHO, COS, BHK, HEK-293, Hela, NIH3T3, VERO, MDCK, MOLT-4, Jurkat, K562, HepG2, etc.

In a preferred embodiment of this invention, the recombinant host cell is Sf9 insect cell.

Suitable culture media and culture conditions for host cells suitable for carrying out DNA recombination techniques are well known in the field of biotechnology. For instance, host cells may be cultured in a fermentation bioreactor, a shaking flask, a test tube, a microtiter plate, or a petri dish, and cultivation of the host cells may be conducted under conditions suitable for growth of said cells, including the culture temperature, the pH value of the culture medium, and the dissolved oxygen concentration of the culture.

Lastly, this invention provides a primer pair for the cloning of a WSSV immediate early promoter-regulatory region, comprising a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16. The primer pair may be used to clone WSSV immediate early promoter-regulatory regions that are evolutionarily homologous to the specific sequences described herein.

It is contemplated that all materials and methodologies described herein may be used for practicing this invention.

This invention will be further described by way of the following examples. One of ordinary skill in the art is familiar with many techniques and teachings allowing the modification of these examples and the examples noted throughout this disclosure that would also employ the basic, novel, or advantageous characteristics of the invention. Thus, the scope of this invention is not limited by the particular examples listed here or elsewhere.

EXAMPLES

I. Materials and Methods

Viral Gene Microarray—Chip Preparation

The *Penaeus monodon* WSSV 1994 Taiwan isolate (WSSV T-1), the genome of which was deposited in the NCBI database under accession no. AF440570, was used in all the experiments described below. This WSSV T-1 isolate was deposited in the China Center for Type Culture Collection (CCTCC, Wuhan University, Luo Jia Shan, Wuhan, Hubei, 430072, People's Republic of China) under the Budapest Treaty on Jan. 11, 1996, and was given accession number CCTCC-V96001 (see U.S. Pat. Nos. 5,824,535 and 6,190, 862 issued to Guang-Hsiung Kou et al.).

WSSV viral gene microarrays (chips) were designed based on the genome of the WSSV T-1 isolate. Briefly, each chip contains 532 predicted WSSV ORFs and a partial sequence of *P. monodon* β-actin gene. After conducting polymerase chain reaction (PCR) using specific primers derived from these 532 ORFs, PCR products with amplicon sizes of 200 to 600 bp were spotted on precoated glass slides (U-Vision Biotech Inc., Taiwan) in triplicate for each WSSV ORF, and with 3 replications for the shrimp (*P monodon*) β-actin gene. The shrimp β-actin gene acted as a positive control and was used to normalize the data across slides.

Details of preparation of viral microarrays are described in various literature, see, e.g. H.-C. Wang, et al. "DNA microarrays of the white spot syndrome virus genome: genes expressed in the gills of infected shrimp," Marine Biotechnology, in press.

Viral Gene Microarray—Target Preparation

Protocols for the preparation of viral inocula and the virus challenge trials are described in M.-F. Tsai et al. (1999), *Dis. Aquat. Org.*, 38 (2), 107-114.

Cultivated WSSV-free shrimps (*P. monodon*) for conducting the CHX (Sigma) treatment and the virus challenge trial were kindly provided by Tung-Kang Marine Laboratory, Taiwan Fisheries Research Institute. During experiments, shrimps with a body weight of 35-45 grams were cultivated in eight 1000 liter FRP (fiber reinforced plastic) tanks containing sterile 33 ppt (parts per thousand) sea water at an ambient temperature of 25° C.

WSSV inocula were prepared from pooled tissues of experimentally infected shrimps (*P. monodon*). To identify WSSV IE genes, the WSSV T-1 infected shrimps were treated with different doses of CHX (12.5 mg/kg, 62.5 mg/kg and 250 mg/kg of body weight, prepared in 20% ethanol) by intramuscular injection 2 h before the virus challenge trial. Control shrimps were injected with 20% ethanol only.

In the virus challenge trials, the CHX and 20% ethanol pretreated shrimps were either mock-infected with a 0.9% NaCl solution or infected with a WSSV inocula (prepared in 0.9% NaCl solution) at a dose of 50 μL per 10 g of body weight by intramuscular injection, respectively. Since gill tissues are one of the main targets of WSSV infection (C.-F. Lo, et al. (1996), *Dis. Aquat. Org.*, 27, 215-225; and H.-C. Liu, et al. (1997), *Dis. Aquat. Org.*, 30, 53-72), gill tissues of the mock-infected and WSSV-infected shrimps were collected at 8 hours post infection (hpi) and immediately frozen in liquid nitrogen until RNA extraction.

Total RNAs were harvested from the collected shrimp gill tissues using an RNeasy kit (Qiagen) according to the manufacturer's protocol. To make cDNA targets, RNA samples (20 μg) were fluorescently labeled with Cy3dUTP using a CyScribe First-Strand cDNA Labeling kit (Amersham Bioscience) according to the manufacturer's instructions. Thereafter, unincorporated free nucleotides were removed using Microcon YM-30 columns (Amicon). The thus-obtained Cy3-labeled cDNAs were condensed and used as microarray targets in subsequent experiments.

Viral Gene Microarray—Probe/Target Hybridization, Scanning and Statistical Analysis The above-prepared Cy3-labeled cDNA targets were subjected to hybridization with all the DNA spots in the WSSV microarrays, followed by scanning the microarrays using a confocal laser scanner (GeneTAC™ LS IV Microarray Scanner, Genomic Solutions). The scanned fluorescence intensities were quantified by GenePix 3.0 (Axon Instruments).

With respect to those transcripts that bound to the microarray probes, their detected signal intensities were converted to approximate measures of absolute expression by subtracting background signal levels. Signal levels of the positive control (*P. monodon* β-actin gene) were used to normalize viral gene expression results across different arrays. WSSV gene expression was determined by plotting the normalized gene expression levels on the CHX-pretreated WSSV-infected chips against the normalized ratios for the corresponding genes in mock-infected chips.

Confirmation of Microarray Results by RT-PCR Analysis of CHX-Insensitive Genes

For the microarray results at the highest level of CHX treatment (250 mg/kg of body weight), those ORFs for which the median level of intensity in the WSSV-infected samples was at least 1.5 fold greater than that in the mock-infected samples were subjected to reverse transcriptase PCR (RT-PCR).

In the RT-PCR analysis, templates were prepared from samples of the original batches of total RNA (i.e. from the 250 mg/kg CHX-pretreated WSSV-infected shrimps) and from an additional batch of RNA extracted from WSSV-challenged shrimps that were pretreated with 20% ethanol. The RNA samples (20 µg) were treated with RNase-free DNase I (Roche) at 37° C. for 1 h to eliminate any viral genomic DNA contamination in the prepared total RNA samples. An aliquot (~10 µg) of total RNA was used to synthesize the first-strand cDNA by using Superscript II reverse transcriptase (Invitrogen) and oligo(dT) primer in a 20 µL reaction mixture. After RT reaction, an aliquot (2 µL) of the reaction product (containing about 1 µg of cDNAs) was subjected to PCR with pairs of specific primers corresponding to those WSSV genes that were expressed in the CHX-pretreated infected shrimps (i.e., the IE gene candidates as shown in the microarray analysis results). As a positive control for CHX treatment, PCR was also run with a gene-specific primer pair dnapolF/dnapolR (Table 1), which were designed based on a previously reported WSSV delayed early gene, dnapol (L.-L. Chen et al. (2002), *Virology*, 301, 136-147).

As a quality control to check for WSSV genomic DNA contamination, PCR was also performed on CHX-pretreated WSSV-infected RNA samples that were not subjected to reverse transcription. PCR products amplified from WSSV genomic DNA served as a PCR-positive control and were also used as a relative size marker.

Promoter Activity Assay

For each of the WSSV IE gene candidates that was confirmed by RT-PCR, a transient reporter assay was performed. For this assay, Sf9 insect cells (Invitrogen) were transfected with a plurality of promoter assay plasmids respectively carrying a EGFP reporter gene therein.

As a starting point in this assay, a plasmid pIZΔIE/V5-His was modified from a commercially available plasmid pIZ/V5-His (Invitrogen) by deleting the OpIE2 (OpMNPV ie2) promoter located in front of the multiple cloning sites (MCS). Subsequently, an EGFP gene (BD Biosciences) was inserted into the MCS of pIZΔIE/V5-His to produce a first derived plasmid pIZΔIE/V5-EGFP-His.

Thereafter, part (~1 kbp) of the 5' untranslated regions (5' UTRs) of each WSSV IE gene candidate was amplified from the WSSV genomic DNA by PCR with primers containing appropriate restriction endonuclease recognition sites at the 5' ends thereof (see Table 2). Each of the resultant PCR products was separately purified using the GFX PCR product purification kit (Roche), digested with restriction endonucleases, and then inserted into the pIZΔIE/V5-EGFP-His MCS in front of the EGFP gene. The resultant plasmids were designated pIZΔIE/WSSVx/V5-EGFP-His, where "x" represents an ORF selected by the RT-PCR assay.

A plasmid pIZ/V5-EGFP-His, which was constructed by cloning the EGFP gene into the plasmid pIZ/V5-His, served as positive control plasmid, whereas a corresponding ΔIE plasmid, i.e. pIZΔIE/V5-EGFP-His, served as a negative control. Another negative control plasmid was constructed by inserting the EGFP gene and the WSSV dnapol promoter region into the plasmid pIZΔIE/V5-EGFP-His to produce pIZΔIE/WSSVdnapol/V5-EGFP-His. For a promoter sequence candidate that gave a positive signal, the reversed sequence thereof was used to construct an additional control plasmid designated as pIZΔIE/WSSVxrev/V5-EGFP-His.

Lastly, in addition to these 1 kbp forward and reverse plasmids, whenever a plasmid expressed a high level of EGFP, its promoter was further analyzed by constructing an EGFP-reporter plasmid driven by a 2 kbp forward fragment.

TABLE 1

Primers used in screening WSSV IE genes by microarray and CHX treatment

| ORF/Gene | Primer sequences | | WSSV T.1 genomic sequence coordinates | Amplicon size (bp) |
|---|---|---|---|---|
| ORF126/ie1 | 1261: gactctacaaatctctttgcca | (SEQ ID NO:1) | 65729 → 65750 | 502 bp |
| | 126SP1: ctacctttgcaccaattgctag | (SEQ ID NO:2) | 66209 ← 66230 | |
| ORF242/ie2 | 242F1: ataccaacaaccccagaa | (SEQ ID NO:3) | 131117 → 131134 | 233 bp |
| | 242R1: atggggcgggatacaaaa | (SEQ ID NO:4) | 131332 ← 131349 | |
| ORF418/ie3 | 418F1: gctggaggaggcttgttgat | (SEQ ID NO:5) | 242832 → 242851 | 269 bp |
| | 418R1: gggccagaaatgccttacag | (SEQ ID NO:6) | 243081 ← 243100 | |
| DNA pol | dnapolF: tgggaagaaagatgcgagag | (SEQ ID NO:7) | 26292 → 26311 | 586 bp |
| | dnapolR: ccctccgaacaacatctcag | (SEQ ID NO:8) | 26858 ← 26877 | |
| VP28 | vp28F: ctgctgtgattgctgtattt | (SEQ ID NO:9) | 278914 → 278933 | 555 bp |
| | vp28R: cagtgccagagtaggtgac | (SEQ ID NO:10) | 279450 ← 279468 | |
| Intergenic | IC-F2: cagactattaatgtacaagtgcg | (SEQ ID NO:11) | 126597 → 126619 | 1126 bp |
| | IC-R3: gaatgattgttgctggttagaacc | (SEQ ID NO:12) | 125494 ← 125517 | |
| Shrimp β-actin | actinF1: gaygayatggagaagatctgg | (SEQ ID NO:13) | — | 686 bp |
| | actinR1: ccrgggtacatggtggtrcc | (SEQ ID NO:14) | | |

The veracity of all these clones was confirmed by DNA sequencing. The primers used for the construction of these plasmids are listed in Table 2.

ucts were cloned into pGEM-T Easy vector (Promega) and sequenced. The sequences of the inserts were compared with the WSSV genomic DNA sequence.

TABLE 2

Primers used for constructing transient expression vectors for the promoter activity assay

| Plasmid | Primer sequences (5'-3')/restriction enzyme* | | Amplicon size (bp) |
|---|---|---|---|
| pIZΔIE/WSSV126-1k/V5-EGFP-His | F: cggaattcgagatcctagaaagaggagtg<br>R: ccgctcgagcttgagtggagagagagagc | (SEQ ID NO:15)/EcoR1<br>(SEQ ID NO:16)/Xho1 | 997 |
| pIZΔIE/WSSV126-2k/V5-EGFP-His | F: cggaattcgatgatggtgatgtttctagg<br>R: ccgctcgagcttgagtggagagagagagc | (SEQ ID NO:17)/EcoR1<br>(SEQ ID NO:16)/Xho1 | 2063 |
| pIZΔIE/WSSV126rev/V5-EGFP-His | F: cggaattccttgagtggagagagagagc<br>R: ccgctcgaggagatcctagaaagaggagtg | (SEQ ID NO:18)/EcoR1<br>(SEQ ID NO:19)/Xho1 | 997 |
| pIZΔIE/WSSV242/V5-EGFP-His | F: ggggtaccgtcttcaacatcttcttgttcg<br>R: ataagaatgcggccgccatgaagatctctgggaaatg | (SEQ ID NO:20)/Kpn1<br>(SEQ ID NO:21)/Not1 | 987 |
| pIZΔIE/WSSV418/V5-EGFP-His | F: cggaattcgtcgcacatgtgtctaaacttc<br>R: ccgctcgagcaacaagcctcctccagcc | (SEQ ID NO:22)/EcoR1<br>(SEQ ID NO:23)/Xho1 | 841 |
| pIZΔIE/WSSVdnapol/V5-EGFP-His | F: tagagctcacttctcctgacactcttgactgat<br>R: gtggaagagggtgatggagctggagatgatcatc | (SEQ ID NO:24)/Sac1<br>(SEQ ID NO:25) | 571 |

*The restriction enzyme cutting sites of the primers are underlined.

For DNA transfection, Sf9 insect cells were seeded into a 24 well plate ($3\times10^5$ cells/well) and grown in Sf-900 II SFM serum-free medium (Invitrogen) overnight at 27° C. Plasmid DNA was diluted to 1 μg/μL in TE buffer (pH 8.0), and liposome mediated transfection of the Sf9 cells (1 μg of plasmid DNA per well) was carried out using the Cellfectin Reagent (Invitrogen) according to the manufacturer's instructions. At 72 h after transfection, EGFP fluorescence signals were observed under an Olympus IX71 inverted fluorescence microscope and photographically recorded using an Olympus DP50 digital microscope camera. At that time, cells were harvested and lysed.

The thus-obtained cell lysate from each well was adjusted to an equal amount of total protein and assayed for EGFP by Western blotting. For the Western blots, the total proteins of each cell lysate were separated on 15% SDS-PAGE, transferred to a PVDF membrane (Osmonics), and probed using either anti-EGFP monoclonal antibody (B-2, Santa Cruz Biotechnology) or anti-human β-actin polyclonal antibody (H-196, Santa Cruz Biotechnology). The blots were developed using an enhanced chemiluminescent-light (ECL) detection kit (NEN Life Sciences), in which goat anti-mouse IgG or goat anti-rabbit IgG conjugated with horseradish peroxidase was used as a secondary antibody.

Mapping the 5' and 3' Termini of Immediate Early Gene Transcripts

The 5' and 3' regions of the immediate early gene transcripts were obtained by rapid amplification of the cDNA 5'/3' ends (M. A. Frohman et al., (1988), *Proc. Natl. Acad. Sci. USA*. 85, 8998-9002) using a commercial 5'/3' RACE kit (Roche) with an avian myeloblatosis virus (AMV) reverse transcriptase (Roche, included in the kit). The RNA samples used for 5'/3' RACE analysis in this study were isolated from the shrimps at 24 h after WSSV infection and then treated with RNase-free DNase I (Roche). The appropriate gene-specific primers used for rapid amplification of the cDNA 5'/3' ends are listed in Table 3. The final amplification prod-

TABLE 3

Specific primers used for ORF126 5' RACE and 3' RACE

| | Primer sequences (5'-3') | Usage |
|---|---|---|
| 126SP1: | ctacctttgcaccaattgctag<br>(SEQ ID NO:2) | 5' RACE |
| 126SP2: | gtacagtactgtccatgtcgat<br>(SEQ ID NO:26) | 5' RACE |
| 126SP3: | cctcttcatcacctcaatacc<br>(SEQ ID NO:27) | 5' RACE |
| 128SP1: | gagactgatcgacatggacagtac<br>(SEQ ID NO:28) | 3' RACE |

Temporal Analysis of WSSV Immediate Early Gene Transcripts by RT-PCR

WSSV-challenged shrimps (*P. monodon*) were sampled at 0 (i.e. immediately before infection), 2, 4, 6, 8, 12, 18, 24, 36, 48, 60 and 72 hpi. Total RNA was extracted from pleopods of the harvested shrimps at each time point, purified with TRIzol Reagent (Invitrogen) and then treated with RNase-free DNase I (Roche) to remove any residual DNA. First strand cDNA synthesis was performed using the oligo(dT) primer, and 2 μL (~1 μg) of the cDNA was subjected to PCR in a 50-μL reaction mixture containing an appropriate primer pair (see Table 1). For comparison, the WSSV dnapol and vp28 gene fragments were also amplified from the same templates by the primer pairs dnapolF/dnapolR and vp28F/vp28R, respectively. A shrimp β-actin primer set, actinF1/actinR1, was used as an internal control for RNA quality and amplification efficiency. To confirm that there was no WSSV DNA contamination in the RNA samples, a WSSV genomic DNA-specific primer pair, IC-F2/IC-R3, derived from an intergenic region of the WSSV genome, was also used as a quality control. The primer sets used to amplify the target ORF/gene sequences are listed in Table 1.

Analysis of Immediate Early Gene Promoter and Coding Regions

Based on the genome of WSSV T-1 (NCBI accession no. AF440570), the nucleotide sequences of the ORFs and the regions upstream of the ORFs were analyzed using the computer program NNPP (Reese, M. G., EecKman, F. H., 1995. New neural network algorithms for improved eukaryotic promoter site recognition. In: The seventh international genome sequencing and analysis conference. Hilton Head Island, S. C.; M. G. Reese, et al. (1996), Large scale sequencing specific neural networks for promoter and splice site recognition. In: Hunter, L., Klein. T. E. (Eds.), Biocomputing: Proceedings of the 1996 Pacific symposium. World Scientific Publishing, Singapore), and the GenBank/EMBL, SWISSPROT, PIR and EMBOSS databases.

II. Results

Screening for WSSV IE Genes Using Microarrays and CHX Treatment

When the WSSV DNA (ORF/gene) microarrays were used to examine viral gene expression, the presence of the protein synthesis inhibitor CHX in the WSSV-infected shrimps was expected to lead to specific accumulation of RNA transcripts of viral immediate early genes. This is because, while the transcription of all other viral genes requires viral proteins as transcription factors, synthesis of such proteins would have been inhibited due to the presence of CHX.

FIG. 1 shows scatterplots of normalized Cy3 florescence intensities (i.e. expression levels) for the 532 WSSV ORFs on the microarrays under conditions of WSSV infection versus mock infection in three virus challenge trials with different doses of CHX (12.5 mg/kg, 62.5 mg/kg and 250 mg/kg). Each plotted point is based on triplicate microarray results, corresponds to a single WSSV ORF, and represents the ratio of Cy3 fluorescence levels to β-actin expression levels. Proximity to the 45° line of equivalence indicates similar levels of expression under both infected and non-infected conditions. The differential expression cut-off line (1.5:1) is shown in panel C of FIG. 1.

As can be seen from FIG. 1, in the presence of increasing doses of CHX, the differential expression levels of the WSSV genes increasingly approach the 45° line of equivalence. The observed results not only evidence that the CHX treatment successfully inhibited viral protein synthesis but also suggest that, for most of these 532 WSSV ORFs, WSSV gene transcription does indeed depend on the presence of one or more viral proteins.

ORFs that were relatively unaffected by the highest CHX dosage (i.e. had a differential expression level greater than 1.5:1) were considered to be candidates for IE genes. Although data points near the origin of the scatterplots cannot clearly be distinguished, computer analysis identified 60 IE gene candidates from panel C of FIG. 1.

RT-PCR Analysis of CHX-Insensitive Genes

Figure 2:
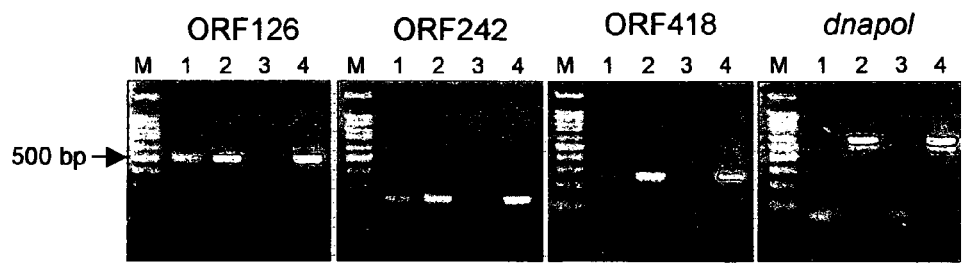
FIG. 2 shows the agarose gel electrophoresis RT-PCR results for the ORFs of three WSSV IE gene candidates (ORF126, ORF242, ORF418) and the WSSV DNA polymerase gene (dnapol)(positive control), in which M: 100 bp DNA ladder (Lambda Biotech Inc., Taiwan); lane 1: RT-PCR product of 250 mg/kg CHX-pretreated group; lane 2: RT-PCR product of vehicle-pretreated group (20% ethanol only); lane 3: PCR product of 250 mg/kg CHX-pretreated group; and lane 4: PCR product amplified from WSSV genomic DNA (amplicon size reference)

The 60 IE gene candidates as identified above were further subjected to RT-PCR analysis. FIG. 2 shows the agarose gel electrophoresis RT-PCR results for the ORFs of three WSSV IE gene candidates (ORF126, ORF242, ORF418), in which the WSSV DNA polymerase gene (dnapol) was used as a control, the primer sets used to amplify the target ORF/gene sequences are listed in Table 1, and the results were based on total RNAs extracted from the gills of WSSV-infected shrimps at 8 hpi. Lane 1 'shows the RT-PCR results of the 250 mg/kg CHX-pretreated group; lane 2 shows the RT-PCR results of the vehicle-pretreated group (20% ethanol only); lane 3 shows the PCR results of the 250 mg/kg CHX-pretreated group that was not subjected to reverse transcription; lane 4 shows the PCR product amplified from WSSV genomic DNA (PCR positive control); and lane M is the 100 bp DNA ladder (Lambda Biotech Inc., Taiwan).

The obtained results identified three CHX-insensitive ORFs, i.e. ORF126, ORF242, and ORF418. Repeated checking of total RNA samples from different individual WSSV-infected shrimps confirmed that such CHX-insensitivity as observed in FIG. 2 was consistent. The possible sequence coordinates of these three ORFs in the genomes of three known WSSV isolates are summarized in Table 4. It can be seen that no deletion of any one of these three ORFs occurs in the three known WSSV isolates.

TABLE 4

Sequence coordinates of three identified CHX-insensitive ORFs in the genomes of three known WSSV isolates.

| | Taiwan isolate (WSSV T-1)* NCBI Accession No. AF440570 | Thailand isolate** NCBI Accession No. AF369029 | China isolate*** NCBI Accession No. AF332093 |
| --- | --- | --- | --- |
| ORF126 | 65711~66385 | 81077~81751 | 32125~32799 |
| ORF242 | 131023~131349 | 146706~146380 | 97436~97762 |
| ORF418 | 242850~243032 | 256954~257136 | 207904~208086 |

*isolated from infected *Penaeus monodon* shrimp in Taiwan, the complete genomic sequence thereof was directly submitted to the GenBank for deposit; and the term "T-1 strain" was first described in L.-L. Chen et al. (2002), Virology 301, 136-147.
**isolated from infected *Penaeus monodon* shrimp imported from Thailand in 1996, see Mariëlle C. W. van Hulten et al., Virology. Jul. 20, 2001, 286 (1): 7-22"
***isolated from infected *Penaeus japonicus* shrimp in Tongan, Xiamen, east China, in October 1996, see Feng Yang et al., J. Virol.. December 2001, 75 (23): 11811-11820°

Promoter Activity Assay for WSSV IE Gene Candidates

Figure 3:
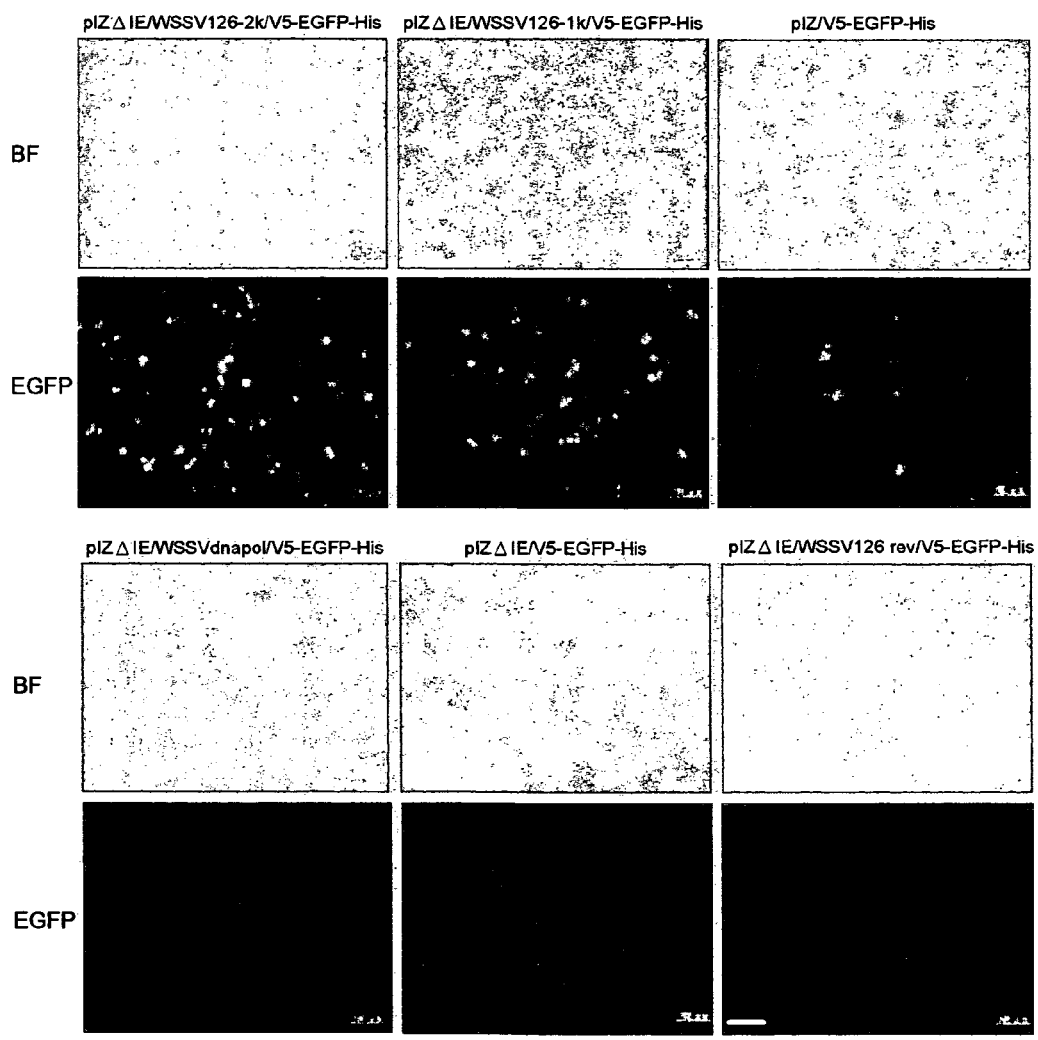
FIG. 3 shows the promoter activities for WSSV IE gene candidates in Sf9 insect cells transfected with the indicated plasmids for 72 h, in which the cells were examined at brightfield (BF panel) and darkfield (EGFP panel, to observe the presence/absence of green fluorescence); scale bar=100 μm.

Referring to FIG. 3, at 72 h post transfection, green fluorescent signals generated by the expressed EGFP (enhanced green fluorescent protein) were observed only in Sf9 cells transfected with either pIZΔIE/WSSV126-1k/V5-EGFP-His or pIZΔIE/WSSV126-2k/V5-EGFP-His, both recombinant plasmids being constructed to respectively contain the I kbp and 2 kbp promoter sequences of WSSV ORF126 according to this invention, and in Sf9 cells transfected with the positive control plasmid (pIZ/V5-EGFP-His).

Plasmids that were constructed to respectively contain the promoter sequences of the other two WSSV IE gene candidates, i.e. pIZΔIE/WSSV242/V5-EGFP-His and pIZΔIE/WSSV418/V5-EGFP-His, gave negative results in the Sf9 insect cells transfected thereby (data not shown).

Figure 4:
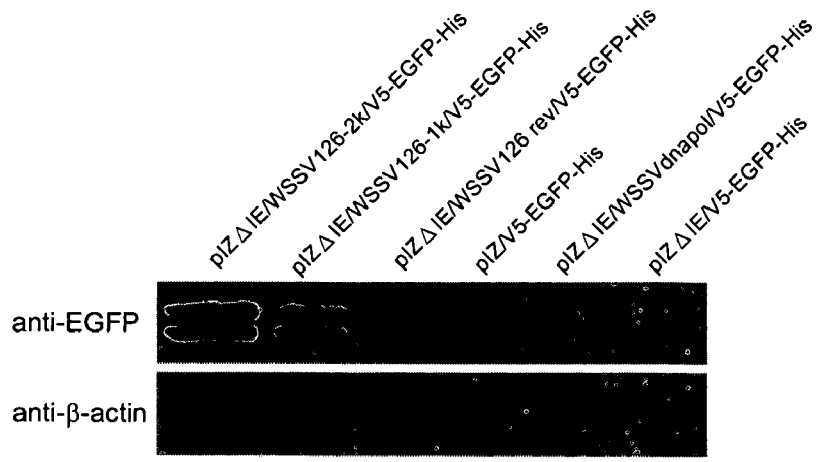
FIG. 4 shows the Western blotting results of SDS-PAGE separated cell lysates from the same transfected Sf9 insect cells of FIG. 3, in which the blotted total proteins of the cell lysates were probed using either anti-EGFP or anti-β-actin (control) antibodies and developed by an ECL chemiluminescence system.

ORF126 was therefore designated as WSSV ie1 (immediate early gene #1). It was also surprising to observe that both the 1 kbp and 2 kbp promoter sequences of the WSSV ie1 gene produced higher EGFP fluorescent signals than the positive control plasmid pIZ/V5-EGFP-His, which contained the promoter of insect virus OpMNPV (Orgyia pseudotsugata multicapsid nuclear polyhedrosis virus) ie2 gene, i.e. the OpIE2 promoter (see FIG. 3). Similar results were also found in the Western blot analysis (FIG. 4). In addition, consistent results were observed in repeated runs of these two different promoter activity assays (data not shown).

It is also observed from FIG. 3 that no green fluorescent signal was generated in Sf9 insect cells transfected with plasmid pIZΔIE/WSSV126rev/V5-EGFP-His, which was constructed to contain the reverse sequence of 1 kbp promoter sequences of WSSV ORF126. This fact suggests that that the promoter of the WSSV ie1 gene is preferably operatively connected to a target gene in forward orientation.

Mapping of the 5' and 3' Termini of the ie1 Transcript

Analysis of the 5' RACE products cloned in the pGEM-T Easy vector revealed that in 6 of the first 7 randomly picked clones, the 5' termini were located 52 nt (G) upstream of the putative ATG initiation codon, while in the other clone, the 5' terminus was at 51 nt (T)(FIG. 5). This suggested that the −52 nt G represents the major transcriptional start point. Upstream (−26 nt) of the transcriptional initiation site (at −82 nt to −78 nt relative to the ATG translational start), a putative TATA box (TATAA) was found. NNPP (Neural Network for promoter prediction) analysis of upstream sequences of the ie1 putative transcription start site identified a high-probability predicted basal promoter region between −92 nt and −43 nt in front of the putative translation start codon (FIG. 5).

In addition, sequence analysis of the cloned 3' RACE products revealed that poly (A) was added at a site 17 nt downstream of the AATAAA polyadenylation signal (FIG. 5).

FIG. 6 shows that a very similar 5' UTR pattern is also found for the WSSV dnapol gene (L.-L. Chen et al. (2002), Virology 301, 136-147), and the WSSV rr1 and rr2 genes (M.-F. Tsai et al. (2000), Virology 277, 92-99). Since the transcription initiation sites of these four genes all conform to the arthropod initiation motif,. i.e. (A/C/T)CA(G/T)T (L. Cherbas and P. Cherbas (1993), Insect Biochem. Mol. Biol., 23, 81-90), it can be reasonably concluded that all of these viral genes have basal elements for transcription that allow them to be transcribed by at least arthropod host RNA polymerase II.

Temporal Analysis of WSSV ie1 Gene Transcription by RT-PCR.

Figure 7:
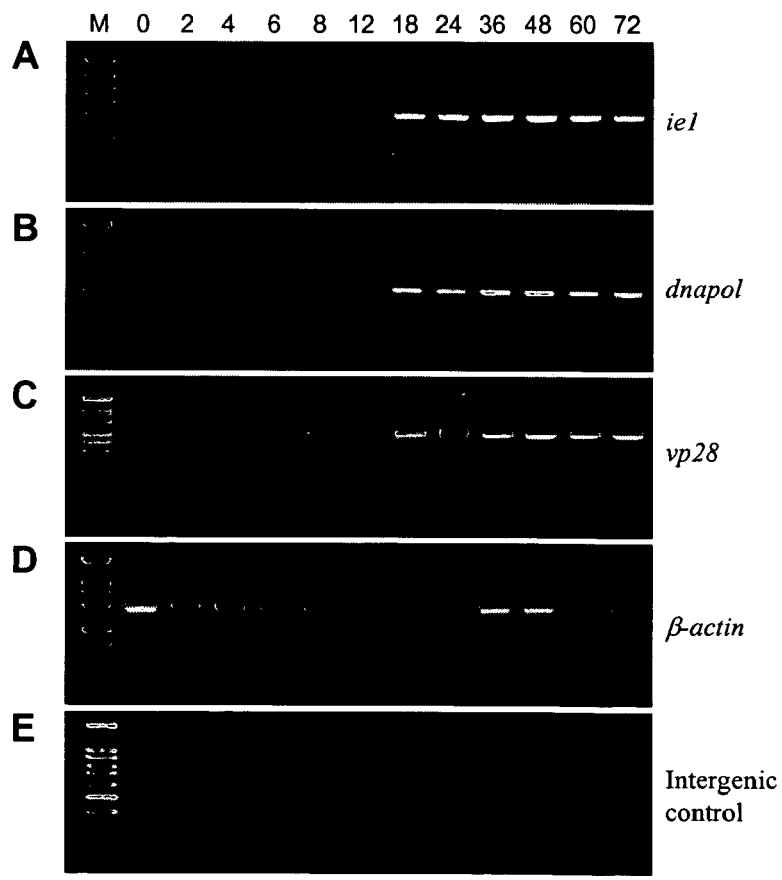
FIG. 7 shows the results of the temporal transcription analysis of WSSV ie1 by RT-PCR, in which ie1-specific primers 126F/126SP1 (panel A), dnapol-specific primers (panel B) and (C) vp28-specific primers (panel C) were used, and shrimp β-actin-specific primers (panel C) and intergenic primers IC-F2/IC-R3 (panel E) were used as internal controls, respectively; lane M is a 100 bp DNA ladder (Lambda Biotech Inc., Taiwan), and the numerals marked on other lanes represent the periods of transfection time in terms of hpi.

A RT-PCR temporal analysis showed that ie1 transcripts were first detected at 2 hpi and continued to be found through to 72 hpi (FIG. 7). The intensity of the ie1 PCR product band increased over time, reaching a maximum at 18 hpi and continuing at a high expression level thereafter. As a comparison, transcripts of the other two WSSV genes, dnapol and vp28 (a WSSV major envelope protein gene, see J.-H. Leu, et al. (2005), J. Virol., January 2005, 79 (1), 140-149) were not detected until 4 hpi.

III. Discussion

Viral immediate early (IE) genes are expressed immediately after primary infection by, or reactivation of, a virus. This class of genes is defined experimentally by their ability to produce transcripts even in the presence of inhibitors of protein synthesis (F. X. Zhu et al. (1999), J. Virol., 73, 5556-5567).

In this invention, a protein synthesis inhibitor, CHX, was used to pretreat shrimps (P. monodon) before they were challenged with WSSV. Shrimps were injected with three different doses of CHX (12.5, 62.5 and 250 mg per kg of body weight), and as expected, as the dose of CHX increased, the number of expressed WSSV genes was reduced (FIG. 1). However, even at the highest dose of CHX (250 mg/kg body weight, in preliminary tests, unchallenged shrimp treated with this dosage only survived for about 12 h, data not shown), there were still 60 WSSV ORFs that produced relatively high numbers of transcripts in the microarray analysis (panel C of FIG. 1).

RT-PCR reduced the number of IE gene candidates to only three that consistently showed CHX-insensitivity (FIG. 2). A possible reason for the observed high initial number of IE gene candidates (or false positives) may be that in vivo, CHX was unable to synchronously and completely inhibit the expression of all IE genes in every cell, especially for IE genes that had a strong promoter. As a consequence, since the appearance of any viral IE gene transcriptional factor may promptly trigger the downstream gene expression cascade, it is very likely that transcription of delayed early and late genes may also start very soon.

On the other hand, referring to panel C of FIG. 1, it is noted that not only is the 1.5:1 differential expression cut-off criterion somewhat arbitrary, the absolute expression levels are also greatly reduced with an increasing dose of CHX, which makes it more difficult to quantify the fluorescence intensity data accurately. Therefore, it is reasonable to presume that there may still be other IE genes that are not included in the 60 candidates identified in panel C of FIG. 1.

It has been reported in literature that several baculovirus immediate early genes are expressed in a range of insect cell lines early in the virus infection process, and are normally transcribed by the host cell transcriptional machinery across species (D. D. Hegedus et al. (1998), Gene, 207, 241-249; Y. G. Zhao and P. Eggleston (1999), Insect Mol. Biol., 8, 31-38). Accordingly, IE genes may be important in the determination of host range.

To the Applicant's knowledge, WSSV infection in insect cell lines has yet to be documented. However, the WSSV ie1 promoter as identified herein is capable of driving transient EGFP expression in the non-host Sf9 cells (FIG. 3). The WSSV ie1 promoter must therefore share the conserved sequences for invertebrate transcriptional factor recognition.

Accordingly, based on the fact that the WSSV ie1 promoter could be activated even by a non-decapod host transcription factor, it is reasonable to postulate that WSSV is able to infect a wide range of hosts, both crustacean and, possibly, non-crustacean (T. W. Flegel (1997), World J. Microbiol. Biotech., 13, 433-442, D. V. Lightner (1996), A handbook of pathology and diagnostic procedures for disease of penaeid shrimp. World Aquaculture Society, Baton Rough, La.; C.-F. Lo, et al. (1996), Dis. Aquat. Org., 27, 215-225).

With respect to the other two identified CHX-insensitive genes, ie. ORF242 and ORF418, whose promoters failed to drive EGFP expression in the transfected Sf9 cells, it is postulated that some other specific transcriptional factors may be required for these two IE gene candidates' promoters to function. These factors are presumably decapodal, and are absent in Sf9 cells. These two candidates may be shrimp-cell specific and should therefore be assayed in shrimp cells before being ruled out as IE genes.

The TATA motif is the principal regulatory element of many baculovirus early promoters, and consists of an ANT-rich motif located 25-31 nucleotides upstream of the transcription initiator (G. W Blissard and G. F. Rohrmann (1991), *J. Virol.*, 65, 5820-5827; G. W. Blissard et al. (1992), *Virology,* 190, 783-793; J. A. Dickson and P. D. Friesen (1991), *J. Virol.*, 65, 4006-4016; L. A. Guarino and M. W. Smith (1992), *J. Virol.*, 66, 3733-3739, S. S. Pullen and P. D. Friesen (1995), *J. Virol.*, 69, 756-165). The TATA motif and the transcription initiator together are the basal elements of the RNA polymerase II promoter.

The WSSV ie1 promoter region also conforms to this pattern (FIG. 5), which suggest that, like most of the insect baculovirus early genes, WSSV ie1 transcription is mediated by host RNA polymerase II. FIG. 6 shows that WSSV dnapol, rr1 and rr2 also conform to this pattern. Their transcription start sites match the CAGT/CAGT-related motif (L.-L. Chen et al (2002), *Virology*, 301, 136-147; L. Cherbas and P. Cherbas (1993), *Insect Biochem. Mol. Biol.*, 23, 81-90; S. S. Pullen and P. D. Friesen (1995), *J. Virol.*, 69, 3575-3583), and they are located from 25 to 28 nucleotides downstream of the TATA box. This suggests that these three genes should also be transcribed by host RNA polymerase II. However, these genes, which were all inhibited by CHX treatment, were not expressed in the transfection assay (FIG. 3 for dnapol, data not shown for rr1 and rr2). It is therefore presumed that the successful transcription of dnapol, rr1 and rr2 requires the presence of [a] viral protein transcription factor[s], either in addition to, or as a substitute for, the host transcription factors used by RNA polymerase II.

The results of the promoter activity assay (FIG. 3) suggested that the sequences upstream of the WSSV ie1 coding region were very effective in activating gene expression in Sf9 cells. As can be seen from FIG. 8, the 5' UTR (untranslated region) of ie1 includes several sequences that match the consensus sequences of the GATA motif (A/T)GATA(G/A). This is potentially important because the GATA motif is recognized as a binding site for transcription factors, for example in the promoter of the baculovirus OpMNPV IE gene, gp64 (P. H. Kogan and G. W. Blissard (1994), *J. Virol.*, 68, 813-822).

FIG. 8 also shows several other possible regulatory elements, including two direct repeat sequences (CACACACA, positions 2024-2030 of SEQ ID NO:29, and CTCTCTCTCT, positions 2045-2054 of SEQ ID NO:29), the repetition of two short sequences (TTTCTGG and CCAGAAA), the baculovirus early gene promoter motif (upstream regulatory element) (CGTGC)(R. L. Harrison and B. C. Bonning (2003), *J. Gen. Virol.*, 84 (Pt 7), 1827-1842), the baculovirus late promoter initiator (TTAAG)(L. A. Guarino and M. W. Smith (1990), *Virology*, 179, 1-8; T. D. Morris and L. K. Miller (1994), *Gene*, 140, 147-153), and a palindrome sequence that may function as a transcriptional enhancer (C. T McMurray et al. (1991), *Proc. Natl. Acad. Sci. USA.*, 88, 666-670, C. Rasmussen et al. (1996), *Virology*, 224, 235-245).

In particular, since the palindrome sequence is located farther than 1,000 nt upstream of the translation start site, it might help to account for the difference in expression levels between pIZΔIE/WSSV126-2k/V5-EGFP-His and pIZΔIE/WSSV126-1k/V5-EGFP-His in the transfected Sf9 cells (FIG. 3).

On the other hand, the 5' RACE analysis performed on RNA extracted from WSSV-infected shrimps at 24 hpi produced no evidence that the TTAAG baculovirus late promoter initiator ever functioned as an initiator for the transcription of WSSV ie1.

Lastly, BLAST analysis of the GenBank/EMBL, SWISPROT and PIR databases predicted that the ie1 coding region contains the Cys2/His2-type zinc finger motif. This motif has a role in DNA binding and implies that ie1 functions as a transcription factor. Further study should investigate which WSSV genes use ie1 as a transcription factor.

All patents and literature references cited in the present specification as well as the references described therein, are hereby incorporated by reference in their entirety. In case of conflict, the present description, including definitions, will prevail.

While the invention has been described in connection with specific embodiments thereof, it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

What is claimed is:

1. An isolated WSSV immediate early promoter-regulatory region consisting essentially of a nucleotide sequence selected from the group consisting of:
   (i) a nucleotide sequence of SEQ ID NO:29;
   (ii) a 5'-truncated fragment of the nucleotide sequence of (i) which has at least 92 nucleotide residues as calculated from the 3' end of SEQ ID NO:29;
   (iii) a nucleic acid sequence which is amplified from polymerase chain reaction using a WSSV genomic DNA as template and a primer pair having a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16;
   (iv) a nucleic acid analogue of the nucleotide sequence of (i), which has at least about 60% sequence identity to the nucleotide sequence of (i) and is conserved in a region thereof that corresponds to the 92 nucleotide residues as calculated from the 3' end of SEQ ID NO:29, and which can drive the expression of a target gene operatively connected thereto; and
   (v) a nucleic acid analogue of the 5'-truncated fragment of (ii), which has at least about 60% sequence identity to the 5'-truncated fragment of (ii) and is conserved in a region thereof that corresponds to the 92 nucleotide residues as calculated from the 3' end of SEQ ID NO:29, and which can drive the expression of a target gene operatively connected thereto.

2. The isolated WSSV immediate early promoter-regulatory region of claim 1, consisting essentially of a 5'-truncated fragment of the nucleotide sequence (i), wherein the 5'-truncated fragment has at least 160 nucleotide residues as calculated from the 3' end of SEQ ID NO:29.

3. The isolated WSSV immediate early promoter-regulatory region of claim 1, consisting essentially of a 5'-truncated fragment of the nucleotide sequence (i), wherein the 5'-truncated fragment has at least 250 nucleotide residues as calculated from the 3' end of SEQ ID NO:29.

4. The isolated WSSV immediate early promoter-regulatory region of claim 1, consisting essentially of a 5'-truncated fragment of the nucleotide sequence (ii), wherein the 5'-truncated fragment has at least 500 nucleotide residues as calculated from the 3' end of SEQ ID NO:29.

5. The isolated WSSV immediate early promoter-regulatory region of claim 1, consisting essentially of a 5'-truncated fragment of the nucleotide sequence (ii), wherein the 5'-truncated fragment has at least 1000 nucleotide residues as calculated from the 3' end of SEQ ID NO:29.

6. The isolated WSSV immediate early promoter-regulatory region of claim 1, wherein in sub-item (iii), the WSSV genomic DNA to be used as template is extracted from a Taiwan isolate WSSV T-1 deposited in the China Center for Type Culture Collection under an accession number CCTCC-V96001.

7. The isolated WSSV immediate early promoter-regulatory region of claim 1, which is obtained by chemical synthesis.

8. The isolated WSSV immediate early promoter-regulatory region of claim 1, which is obtained by recombinant DNA technology.

9. A recombinant expression vector comprising a first target gene encoding a selected gene product, and an isolated WSSV immediate early promoter-regulatory region as claimed in claim 1 operatively connected to the first target gene.

10. The recombinant expression vector of claim 9, wherein the isolated WSSV immediate early promoter-regulatory region is located upstream of the first target gene in forward orientation.

11. The recombinant expression vector of claim 9, further comprising at least one of the following: a further promoter sequence located apart from the WSSV promoter-regulatory region, a second target gene encoding a second gene product, a transcription starting site, a transcription termination site, a ribosome binding site, a secretion signal coding sequence, a RNA splicing site, a Shine-Dalgarn sequence, a marker gene, a reporter gene, an antibiotic-resistance gene, a translation termination site, an insertion cloning location, an enhancer sequence, a polyadenylation site and a regulatory sequence.

12. The recombinant expression vector of claim 11, wherein the first and second target genes independently encode a gene product selected from the group consisting of enzymes, therapeutic polypeptides, antigenic determinants and antibodies.

13. The recombinant expression vector of claim 9, which is pIZΔIE/WSSV126-2k/V5-EGFP-His.

14. The recombinant expression vector of claim 9, which is pIZΔIE/WSSV126-1k/V5-EGFP-His.

15. A recombinant host cell produced from the transformation of a host cell with a recombinant expression vector as claimed in claim 9.

16. A recombinant host cell according to claim 15, which is selected from the group consisting of bacterial cells, yeast cells, fungal cells, plant cells, insect cells, crustacean cells, non-crustacean animal cells, and human cells.

17. A recombinant host cell according to claim 16, which is Sf9 insect cell.

18. A primer pair for the cloning of a WSSV immediate early promoter-regulatory region, comprising a forward primer and a reverse primer, the forward primer consisting essentially of a nucleotide sequence selected from nucleotide sequences as shown in SEQ ID NO:15 and SEQ ID NO:17, the reverse primer consisting essentially of a nucleotide sequence of SEQ ID NO:16.

19. The isolated WSSV immediate early promoter-regulatory region of claim 1, wherein the nucleic acid analogue of (iv) or (v) includes a region that corresponds to the 92 nucleotide residues as calculated from the 3' end of SEQ ID NO:29.

* * * * *